United States Patent [19]

Rasmussen et al.

[11] Patent Number: 5,712,408
[45] Date of Patent: Jan. 27, 1998

[54] DIAMINOMALEONITRILE DERIVATIVE COMPOUNDS, POLYMERS, AND METHOD OF PRODUCING SAME

[75] Inventors: Paul G. Rasmussen; Sarah E. Reybuck; Taeseok Jang; Richard G. Lawton, all of Ann Arbor, Mich.

[73] Assignee: The Regents of the University of Michigan, Ann Arbor, Mich.

[21] Appl. No.: 709,441

[22] Filed: Aug. 20, 1996

[51] Int. Cl.$^6$ .................................................. C07C 251/12
[52] U.S. Cl. ................................................................ 558/446
[58] Field of Search .................................................. 558/446

[56] References Cited

U.S. PATENT DOCUMENTS

| | | | |
|---|---|---|---|
| 3,912,724 | 10/1975 | Begland | 260/240 G |
| 3,914,276 | 10/1975 | Begland | 260/465 E |
| 3,914,279 | 10/1975 | Begland | 260/465 SR |
| 3,962,220 | 6/1976 | Begland | 260/204 G |
| 3,962,221 | 6/1976 | Begland | 260/240 G |
| 4,002,616 | 1/1977 | Neumer | 260/240 G |
| 4,897,419 | 1/1990 | Heidenreich et al. | 514/523 |

FOREIGN PATENT DOCUMENTS

| | | |
|---|---|---|
| 0312908 | 10/1988 | Germany. |
| 49-127921 | 12/1974 | Japan. |

OTHER PUBLICATIONS

C.B. Pollard and R. F. Parcell, "Synthesis of N-Allylidene-alkylamines," 2925, Jun. 1951.

H.D. Finch, "Reaction with Nitrogen Compounds," Chapter 6 from *Acrolein*, Edited by C.S. Smith, John Wiley & Sons, Inc., New York, 1962.

*Primary Examiner*—Johann Richter
*Assistant Examiner*—Ebenezer Sackey
*Attorney, Agent, or Firm*—Barnes, Kisselle, Raisch, Choate, Whittemore & Hulbert, P.C.

[57] ABSTRACT

The invention provides a compound having conjugated double bonds in an acyclic structure formed by Schiff base reaction between an unsaturated aldehyde (RCHO) and diaminomaleonitrile (DE). The compound is a monoalkylated DAMN derivative having one unit of diaminomaleonitrile for every unit of alkyl (RC) derived from the unsaturated aldehyde. The invention also provides a polymer having an acyclic structure and containing monomeric units formed by Schiff base reaction between an unsaturated aldehyde and a diaminomaleonitrile.

8 Claims, 27 Drawing Sheets

DIAMINOMALEONITRILE DERIVATIVE COMPOUNDS, POLYMERS, AND METHOD OF PRODUCING SAME

FIELD OF THE INVENTION

The present invention relates to compounds and polymers based on derivatives of diaminomaleonitrile and method for preparing same.

BACKGROUND OF THE INVENTION

Diaminomaleonitrile is also referred to as 2,3-diaminomaleonitrile and is the cis isomer as represented by the following formula. The trans isomer of this compound is called diaminofumazonitrile. The cis isomer is the common form and for convenience is referred to by the acronym DAMN.

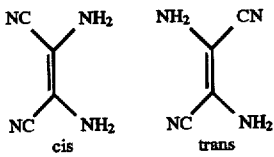

Although the starting geometry of DAMN is known to be "cis", derivatives of DAMN do not necessarily retain the cis orientation. Background concerning DAMN and its cis and trans orientation and that of its derivatives can generally be found in U.S. Pat. No. 4,897,419 to Heidenreich et al. Along with Heidenreich et al, Begland et al in U.S. Pat. Nos. 3,912,724, 3,914,276, and 3,914,279 generally describe the use of .DAMN to synthesize aryl, cyclic, or heterocyclic molecules. For example, bis-anils of DAMN are prepared for use as dyes, for agricultural uses, and as toxins for pest control. Similar to Heidenreich and Begland, Japanese Patent No. 49-127921, disclosure dated Dec. 7, 1974, describes a method for preparing derivatives of DAMN which are salicylidenediaminomaleonitrile, 5-nitrofurfurylidenediaminomaleonitrile, nicotinylidenediaminomaleonitrile, and hexylidenediaminomaleonitrile. These compounds are described as being generally useful as agricultural chemicals. Formation of polymers based on DAMN derivatives is not reported.

In the past, polymers were not known for having good structural thermal stability and low volatility of decomposition products. Many polymers are difficult to make and difficult to use due to the complex nature of the starting materials, reaction processes, and the relative insolubility and/or infusible nature of such polymers rendering them difficult to coat. Currently used flame retardants often rely on additives which contain environmentally undesirable elements, such as halogens. Therefore, it is preferred to have a flame resistant material which is relatively easy to manufacture and coat.

Presently, there is a need for materials with high thermal stability for use under extreme service conditions. There is also a need for improved materials having desired thermal insulation characteristics, and structural thermal set plastics with high flame resistance. Therefore, what is needed is a new class of compounds and polymers formed therefrom, and a new method for their preparation. What is also needed are materials which have relatively low hydrogen content, relatively high nitrogen content, high thermal stability, low flammability, and a high char yield upon pyrolysis, rendering them useful for a variety of applications.

SUMMARY OF THE INVENTION

It is an object of the present invention to provide a new class of compounds based on diaminomaleonitrile derivatives, such compounds having conjugated, regular alternating single and double bonds. Another object is to provide polymers formed from such compounds. It is also an object of the present invention to provide a method for producing the new class derivative polymers based on diaminomaleonitrile. Another object is to provide new polymeric diaminomaleonitrile derivatives which are homopolymers. Still, another object is to provide a method which permits their production from relatively inexpensive precursors, and which is suitable for scale-up to commercial processing.

In accordance with the invention, new compounds and polymers comprising units of such compounds were prepared having representative formulas as shown in the Figures.

The invention provides a compound having conjugated double bonds in an acyclic structure formed by Schiff base reaction between an unsaturated aldehyde (RCHO) and diaminomaleonitrile (DS). The compound, usable as a monomer, is a monoalkylated DAMN derivative having 1 unit equivalent of the diaminomaleonitrile component for every unit of the alkyl (RC) component derived from the unsaturated aldehyde. A polymer is formed from monomeric units of the aforesaid compound. Such polymer also has an acyclic structure, since the polymer contains monomeric units formed by the aforesaid Schiff base reaction between an unsaturated aldehyde and diaminomaleonitrile. In one embodiment, the polymer is formed from such monomeric units by melt polymerization, via Michael addition reaction. Advantageously, melt polymerization or polymerization in a solution is possible. Therefore, the polymer is readily adaptable for commercial application in a variety of forms, including as a coating. Desirably, the compound usable as a polymer precursor is of Formula I:

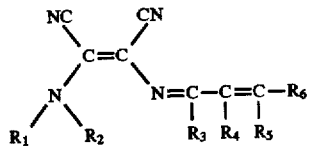

FORMULA I $R_1$, $R_2$, $R_3$, $R_4$, $R_5$, and $R_6$ are identical or different from one another and are each independently selected from hydrogen, and substituted or unsubstituted alkyls. Preferably, such alkyls have 1 to 4 carbons. It is preferred that $R_3$ be hydrogen. It is preferred that at least one of $R_1$ through $R_6$ is selected from the group of alkyls. In one embodiment, one of $R_1$ and $R_2$ is hydrogen. In one embodiment, one of $R_1$ and $R_2$ is an ethyl group and the other one is hydrogen. In one embodiment, one of $R_4$ and $R_5$ is a methyl group and the other is hydrogen; and $R_3$ and $R_6$ are each hydrogen.

In still another embodiment, the invention provides a compound of Formula II:

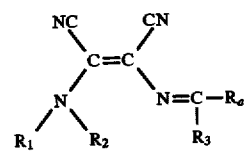

FORMULA II where $R_1$ through $R_3$ are identical or different from one another and are each independently selected from hydrogen, and substituted or unsubstituted alkyls. Preferably, such alkyls have 1 to 4 carbons. Preferably, $R_3$ is hydrogen and $R_a$ is an unsaturated acyclic hydrocarbon containing alternating single and double carbon bonds. The unsaturated acyclic hydrocarbons encompass alkenes and their derivatives. Preferably, among the alternative embodiments described above, the compound is one of the below stated Formulas III, IV, or V referred to respectively as acrodamn (III), crotodamn (IV), and methacrodamn (V). The aforesaid new compounds have the formulas as listed immediately below.

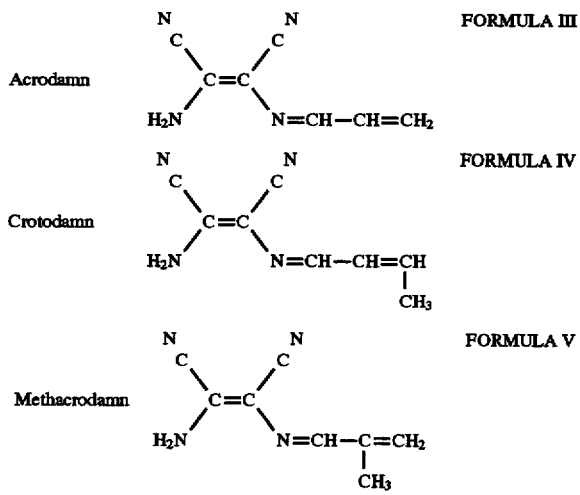

The aforesaid new compounds are usable to form monomeric units for a polymer system having repeating units of Formula II.

In a particularly preferred embodiment, the polymer is formed from monomeric units as designated Formula VI:

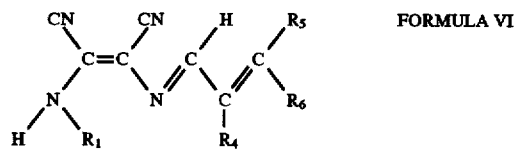

where $R_2$ and $R_3$ are each hydrogen. Such molecules may be combined together to form two repeat units which themselves form repeat units for the polymer according to Formula VII listed immediately below.

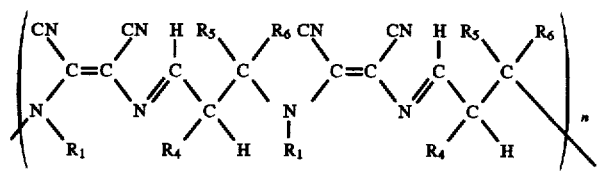

The method for forming such compounds usable as monomeric units for the polymer comprises first forming a cooled solution comprising an unsaturated aldehyde. Preferably, the cooled solution is at a temperature below room temperature and preferably below about 5° C. In one embodiment, the cooled solution is in an ice bath. A second cooled solution is formed comprising diaminomaleonitrile. Advantageously, the second cooled solution is provided at a temperature similar to the requirements for the first cooled solution. The first and second cooled solutions are combined while stirring to react the unsaturated aldehyde with the diaminomaleonitrile to form the monoalkylated diaminomaleonitrile derivative in accordance with the aforesaid Formulas I through VII and such derivative is precipitated out. Next, the polymer is formed from the monomeric compound by a melt polymerization method. Such melt polymerization method is conveniently conducted under ambient conditions by heating to a temperature in a range of about 100° C. to 200° C.; desirably about 110° C. to 160° C.; and preferably in a range of about 120° C. to 150° C. In accordance with the Figures, onset of polymerization occurs for the different derivatives at different points within the broad range. For example, according to a differential scanning calorigram of crotodamn an endothermic peak occurs at about 102° C. indicating melting and an exothermic peak at approximately 145° C. demonstrating polymerization. In the case of methacrodamn, the exothermic peak at 132° C. is due to polymerization. Polymers made by the aforesaid method may be branched or relatively linear polymers depending on substituents carried at the $R_1$ and $R_2$ position. Where $R_1$ and $R_2$ are each hydrogen, a branched polymer generally results. Where one of $R_1$ and $R_2$ carries an alkyl or other "blocking group" a linear polymer results.

In an alternative embodiment for forming a linear polymer, the method comprises providing diaminomaleonitrile having first and second amine groups and reacting the diaminomaleonitrile in solution with acetaldehyde to form a Schiff base reaction product at one amine group at about 0° C. in tetrahydrofuran with stirring preferably in the presence of molecular sieves. The Schiff base reaction product is reduced to provide an ethyl group in place of a hydrogen at the first amine group of the diaminomaleonitrile. Preferably, the reduction is conducted in the presence of borohydride. A first cooled solution is formed comprising the diaminomaleonitrile carrying the ethyl group and a second cooled solution is formed comprising an unsaturated aldehyde. The aforesaid cooled solutions are cooled according to the temperature requirements stated earlier. Preferably, one mole percent acid catalyst, such as hydrogen chloride, is added to one of the solutions and they are combined while stirring to react the diaminomaleonitrile carrying the ethyl group with the unsaturated aldehyde to produce a derivative of diaminomaleonitrile carrying the aldehyde at the first amine; and having a methine carbon of the unsaturated aldehyde double bonded to nitrogen and in place of hydrogen at the second amine group. The diaminomaleonitrile derivative thus formed is precipitated out. A polymer is formed from the aforesaid diaminomaleonitrile derivative by a preferred

FORMULA VII solution process using Anisole (phenylmethylether, methoxybenzene) with refluxing at about 150° C. to 160° C. in the presence of triethyl amine.

The invention provides new compounds and polymers based on such compounds. The monomers contain the highly conjugated regular alternating single and double bonds. Furthermore, the nature of substituent groups may be easily varied to provide various desirable properties such as high thermal stability, solubility, processibility, and conductivity of carbon-nitrogen residues. The invention advantageously provides a relatively straight forward and low cost synthesis method which results in relatively high yields of such desirable compounds and polymers readily adaptable to scale-up for commercial processing.

These and other objects, features, and advantages will become apparent from the following description of the preferred embodiments, claims, and accompanying drawings.

BRIEF DESCRIPTION OF THE DRAWINGS

FIG. 13 is under nitrogen and FIG. 14 is under air.

DETAILED DESCRIPTION OF THE PREFERRED EMBODIMENTS

Figure 1:
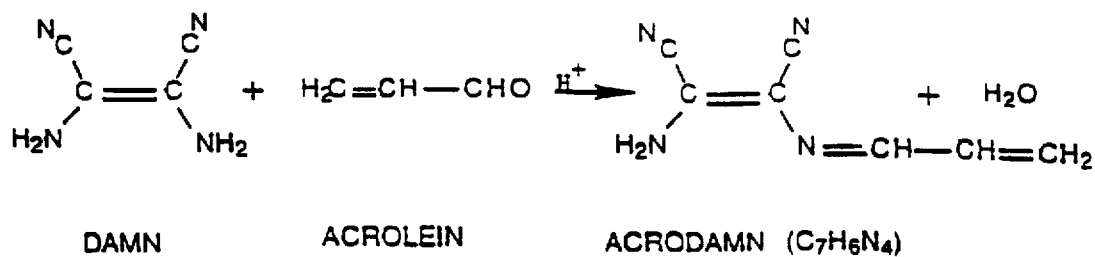
FIG. 1 is an illustration of a basic reaction for preparing N-(cis-1,2,-dicyano-2-aminovinyl)-2-propenimine (acrodamn).
Figure 2:
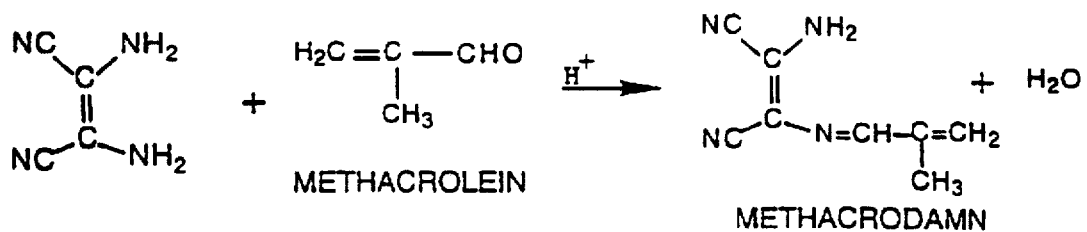
FIG. 2 is an illustration of a basic reaction for preparing N-(cis-1,2-dicyano-2-aminovinyl)-2-methyl-propenimine (methacrodamn).
Figure 3:
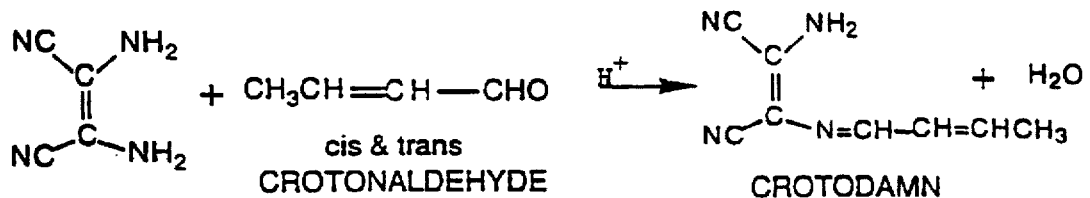
FIG. 3 is an illustration of a basic reaction for preparing N-(cis-1,2-dicyano-2-aminovinyl)-2-butenimine (crotodamn).

It has been discovered that under conditions of low temperature and appropriate combination of reagents, diaminomaleonitrile (DAMN) will react with a slight excess of unsaturated aldehyde to provide Schiff bases in which only one equivalent of DAMN adds to each equivalent of the aldehyde. The invention will be described with reference to examples where DAMN is reacted with acrolein, a substituted acrolein, such as methacrolein or crotonaldehyde. These mono-Schiff base adducts were isolated and characterized and are new compositions of matter. In each case of acrolein, methacrolein, or crotonaldehyde, the new molecules are acyclic. That is, not cyclic, open chains; whereas, when DAMN has been reported to react previously with methyl vinyl ketone, the Schiff base derivative isolated is cyclic. The novel acyclic adducts in the family of the present invention are compounds which readily polymerize under heating or other appropriate catalytic conditions to provide polymers. Key features of the invention which provide, for the first time, the ability to react aliphatic amines with unsaturated aldehydes are: (1) the choice of DAMN as a difunctional amine, which is an aliphatic amine of unusually low basicity due to the electron withdrawing cyano groups; and (2) the choice of low temperature reaction conditions, which suppresses side reactions. The aldehyde is any unsaturated or vinylic aldehyde. Desirably, the aldehyde is a relatively low molecular weight RCHO where R contains 1 to 4 and preferably 1 to 3 carbons. Preferably, the aldehyde is a derivative of acrolein, having substituents at the 2 and/or 3 positions. Preferably, the aldehyde has a 2-methyl and/or 3-methyl substituent. Other alkyls at these positions provide other analogous preferred compounds. Such alkyls are substituted or unsubstituted methyl, ethyl, propyl, butyl, and isopropyl groups and the like. The invention will be described with reference to exemplary formation of monomers which are well characterized crystalline solids of the composition $C_7H_6N_4$ for the acrolein/DAMN adduct, $C_8H_8N_4$ for the methacrolein and crotonaldehyde adducts, and N-ethylDAMN adduct, $C_9H_{10}N_4$. The invention can be understood by the general reactions indicated in FIG. 1 for acrolein, FIG. 2 for methacrolein, and FIG. 3 for crotonaldehyde. Without regard to the geometric structure or the "cis" or "trans" configuration, these compositions have connectivity as illustrated in FIGS. 1 through 3.

The thermal properties of polymers formed from the respective acrodamn (FIG. 1), methacrodamn (FIG. 2), and crotodamn (FIG. 3) monomeric units are outstanding. Melt polymerization of the monomers produced as per FIGS. 1 through 3 occurs at about 120° C. to 140° C. in the melt.

Figure 4:
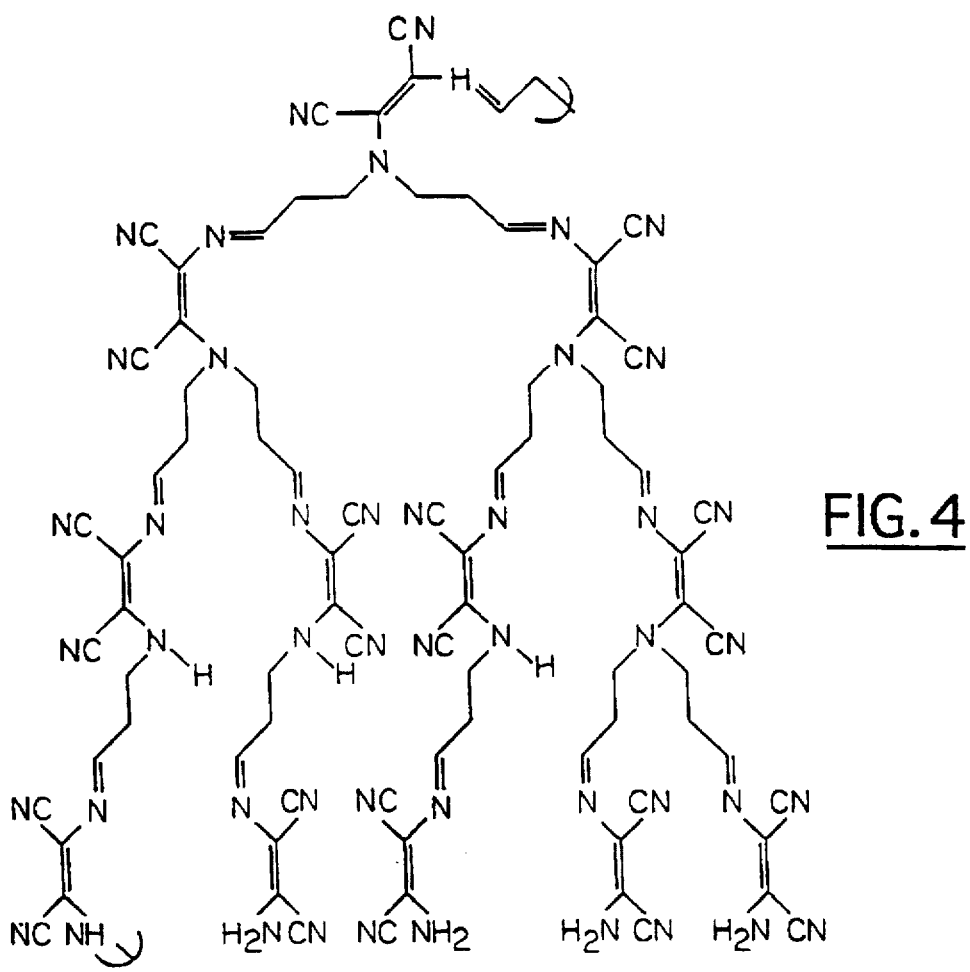
FIG. 4 is an illustration of a polymer formed from monomeric units of acrodamn.

It has been found that the aforesaid acrodamn, methacrodamn, and crotodamn polymerize very rapidly by thermal initiation at relatively moderate temperatures to provide soluble polymers. The polymers may be hyperbranched as shown in FIG. 4 for the acrodamn, methacrodamn, and crotodamn; or the polymers may be relatively linear and relatively free from branching and cross-linking if prepared from N-alkylated DE, or if a blocking group is introduced as described below. The aforementioned Schiff base adducts readily undergo Michael addition reaction from the free amine to the highly activated terminal double bond. This reaction can occur twice for each amine function, creating a monomer of the general category $A_2B$, where each A represents an amine hydrogen which transfers to the beta carbon of the double bond during polymerization. Thus, the resulting polymer structure is hyperbranched with N groups of exclusively primary or secondary amine. This is consistent with an observation of complete loss of vinylic hydrogen in the polymers. This polymerization by Michael addition occurs to provide a yield approaching essentially 100 percent with no small molecule formation or gas evolution. The exemplary structure of the $C_7H_6N_4$ monomer to a polymer $(C_7H_6N_4)_x$ is shown in FIG. 4 (branched polymer). It is possible to avoid branching and to prepare an essentially linear polymer by introducing a blocking group at the amine, then the branching reaction would be blocked and a linear polymer results. A preferred reaction chemistry using monoalkylated DAMN, providing the linear, non-branched polymer, is as per FIG. 5.

The polymer of FIG. 4 has some noteworthy characteristics. At the melt polymerization stage, they are completely soluble in stated organic solvents, such as THF (tetrahydrofuran). Thus, brittle films are easily cast, and the polymer can be readily impregnated into other materials that are solvent permeable. Alternatively, the compressed monomer can be melt polymerized into a shape. This degree of tractability is remarkable in a material that is so adaptable to large scale commercial production.

Derivatives of diaminomaleonitrile as shown in the Figures are prepared according to new process. As to the method of preparation, the compounds of the invention are generically in the classification of Schiff bases. A Schiff base is the product of the condensation of an amine with an aldehyde to form a carbon to nitrogen double bond with the elimination of water. Schiff bases are sometimes called anils, and the carbon bonded doubly to the nitrogen is frequently referred to as a methine carbon. The three compounds described as exemplary, are each best, preferably, prepared by a low temperature synthesis reaction (0° C.) of diaminomaleonitrile (DAMN) a tetramer of HCN, with the selected unsaturated aldehyde in the presence of an acid catalyst. The low temperature reaction should be at a cooled or cold temperature which is below room temperature. Room temperature is taken to range between about 15° C. to 30° C. Desirably, the temperature is 10° C. or less, more desirably 5° C. or less, and preferably provided by an ice bath at about 0° C. or less. The unsaturated aldehydes chosen for exemplary purposes are the acrolein, methacrolein, and crotonaldehydes, as per the Figures. As stated earlier, the acrolein is the parent aldehyde and the methacrolein and the crotonaldehyde are the 2-methyl and 3-methyl derivatives of acrolein. Other alkyl groups at these positions would allow preparation of analogous compounds but it is impractical to illustrate all the examples of this class. Keeping in mind the starting geometry of DAMN is generally taken to be cis, there is no certainty that the derivative polymers retain the cis orientation. In the method of the invention, the condensation reaction is accomplished, for the first time, under low temperature conditions using DAMN and is thought to be controllable in part because the cyano groups on DAMN make the amine functions less than nucleophilic typical amines. The synthesis method will be described in a generic fashion for crotodamn. The same method is applicable to acrodamn and methacrodamn and the lower alkyls as described herein. Characterization data for crotodamn, acrodamn, and methacrodamn is also provided.

A. SYNTHESIS AND CHARACTERIZATION

Example I

N-(cis-1,2-dicyano-2-ethylaminovinyl)-2-butenimine (Crotodamn)

A solution was prepared comprising 3.3 milliliters (40.0 mmol) of crotonaldehyde and 10 drops of 1 molar hydrochloric acid in 40 milliliters of tetrahydrofuran. The solution was cooled to a temperature of approximately 0° C. A second solution was prepared comprising 4.015 grams (37.1 mmol) of diaminomaleonitrile in 100 milliliters of tetrahydrofuran, also cooled to a temperature of approximately 0° C. The diaminomaleonitrile solution was slowly added to the solution containing the crotonaldehyde while stirring. After 5 minutes, the mixed solution was poured over 500 milliliters of ice cold hexane. The resulting precipitate was collected and dried and yielded 3.867 grams of a white, fluffy powder (FIG. 3). The mother liquor was stripped down to give an additional 1.862 grams of a light yellow powder, providing a total yield of approximately 96.5 percent. The powder was recrystallized from ether/hexane to give white/ light yellow powdery crystals. Upon sublimation at reduced pressure, clear yellow needle-shaped crystals were formed.

The product exhibited a melting point of approximately 109° C. to 112° C., infrared characteristics 3457, 3349 (—NH2), 2950 (alkyl), 2239, 2206 (—CN), 1638, 1620, 1606, 1587, 1563, 1370, and 985 cm$^{-1}$. NMR analysis using DMSO solvent revealed δ1.9 (d, 3H), 6.3 (m, 1H), 6.6 (m, 1H), 7.6 (s, 2H , and 7.9 (d, 1H). The calculated product was analyzed to have a formula $C_8H_8N_4$ corresponding to the following weight percents: carbon, 60.0; hydrogen, 5.0; and nitrogen, 35.0. Actual analysis revealed: carbon, 60.8; hydrogen, 5.1; and nitrogen, 33.9, Verifying the formula of the product N-(cis-1,2-dicyano-2-ethylaminovinyl)-2-butenimine (Crotodamn).

Example II

N-(cis-1,2-dicyano-2-aminovinyl)-2-propenimine (Acrodamn)

A similar method of preparation was conducted using the acrolein precursor to prepare N-(cis-1,2-dicyano-2-aminovinyl)-2-propenimine (FIG. 1). This product exhibited infrared pattern at 3416, 3297, 3170 evidencing an amine (—NH2), 2232, 2214 (—CN), 1630, 1587, 1381, 1350, 992, and 965 cm$^{-1}$. NMR analysis conducted in DMSO revealed δ5.9 (d, 1H), 6.1 (d, 1H), 6.6 (m, 1H), 7.9 (s, 2H), and 8.0 (d, 1H). Compositional analysis for the $C_7H_6N_4$ product was calculated on a weight percent basis to be carbon, 57.5; hydrogen, 4.1; and nitrogen, 38.4. Actual analysis revealed: carbon, 57.8; hydrogen, 4.4; and nitrogen, 38.2, evidencing a compound of the formula N-(cis-1,2-dicyano-2-aminovinyl)-2-propenimine (Acrodamn).

Example III

N-(cis-1,2-dicyano-2-aminovinyl)-2-methylpropenimine (Methacrodamn)

A compound designated as N-(cis-1,2-dicyano-2-aminovinyl)-2-methylpropenimine was also prepared utilizing the methacrolein precursor (FIG. 2). The resulting product was found to have a melting point of approximately 118° C. to 120° C. It exhibited infrared values at 3451, 3418, 3306 evidencing an amine (—NH2), 2959 (—alkyl); 2244, 2207 (—CN), 1614, 1595, 1389, 1350, and 909 cm$^{-1}$. Analysis by NMR in DMSO solvent revealed 81.9 (s, 3H), 5.76 (s, 1H), 5.80 (s, 1H), 7.7 (s, 2H), and 7.9 (s, 1H). The product had a calculated general formula of $C_8H_8N_4$ with constituents present in the following weight percents: carbon, 60.0; hydrogen, 5.0; and nitrogen, 35.0. The actual analysis revealed carbon, 60.3; hydrogen, 5.2; and nitrogen 34.3, evidencing a compound of the formula N-(cis-1,2-dicyano-2-aminovinyl)-2-methylpropenimine.

Monomers prepared in accordance with Example I (FIG. 3), Example II (FIG. 1), and Example III (FIG. 2) were polymerized by Michael addition and formed hyperbranched polymers. If it is desired to avoid hyperbranching and obtain a linear polymer, it is preferred that the monomer be formed by a different reaction sequence which is described immediately below.

Example IV

N-(cis-1,2-dicyano-2-ethylaminovinyl)-2-propenimine (N-Ethylacrodamn)

Figure 5:
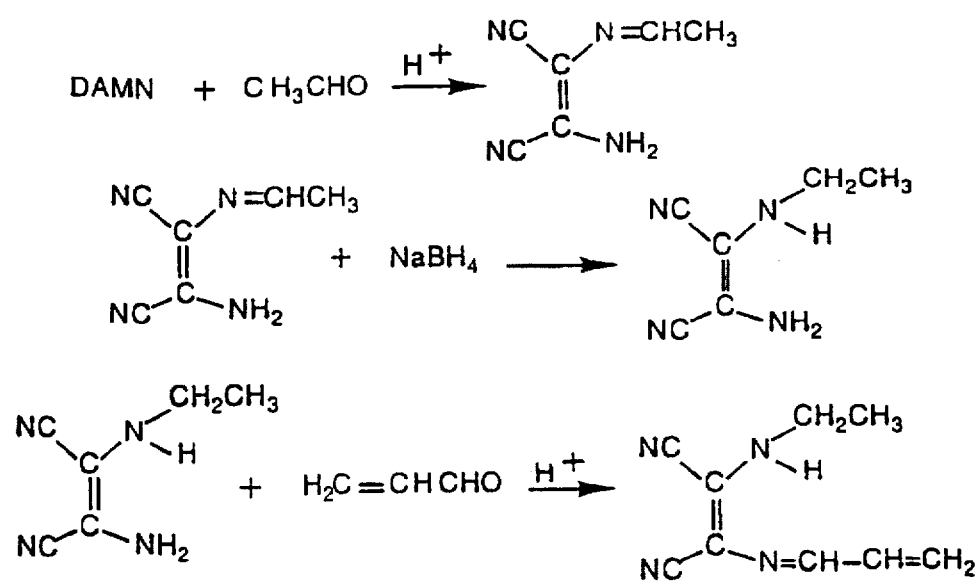
FIG. 5 is an illustration of a general reaction sequence for preparing N-(cis-1,2-dicyano-2-ethylaminovinyl)-2-propenimine (N-Ethylacrodamn).

Compounds (monomeric units) designated as N-(cis-1,2-dicyano-2-ethylaminovinyl)-2-propenimine were prepared according to a reaction sequence as shown in FIG. 5. As shown in FIG. 5, the reaction sequence comprised reacting diaminomaleonitrile with acetaldehyde which forms a Schiff base, followed by borohydride reduction to prepare monoalkylated derivatives. An ethyl blocking group was carried at one of the amines as a result of this borohydride reduction reaction. The diaminomaleonitrile carrying the ethyl blocking group was reacted with an unsaturated aldehyde according to the invention, such as acrolein as shown in FIG. 5, to produce monomeric units N-(cis-1,2-dicyano-2-ethylaminovinyl)-2-propenimine also referred to as N-ethylacrodamn. The last part of the reaction was conducted using essentially two solutions, one containing the acrolein and the other containing the N-Ethyldiaminomaleonitrile prepared by the aforesaid borohydride reduction. More specifically, a first solution was prepared containing 0.17 milliliters (2.5 mmol) of acrolein, 0.350 grams of powdered 4A molecular sieves, and 5 drops of 1 molar hydrochloric acid in 10 milliliters of THF at 0° C. A second solution was prepared comprising 0.308 grams (2.26 mmol) of N-Ethyldiaminomaleonitrile in 10 milliliters of THF at 0° C. The second solution containing the N-Ethyl-diaminomaleonitrile was added to the aforesaid solution containing the acrolein while stirring. Each of the aforesaid solutions, before being combined, was each at 0° C. After 10 minutes the reaction mixture was poured over 200 milliliters of cold hexane. The resulting precipitate was collected, dried, and recrystallized from THF/hexane to give 0.256 grams of yellow needle-shaped crystals corresponding to approximately 65.1 percent yield. The crystals were characterized by a melting point of about 68° C. to 73° C. They were further characterized by exhibiting infrared at 3324 (—NH), 2960 (alkyl), 2194 (—CN), 1622, 1587, 1441, and 1333. An NMR analysis in DMSO solvent revealed δ1.2 (m, 3H) , 3.4 (m, 2H) , 5.9 (d, 1H), 6.1 (d, 1H), 6.6 (m, 1H), 8.0 (d, 1H), and 8.2 (s, 1H).

Monomer and Polymer Characteristics

Figure 6:
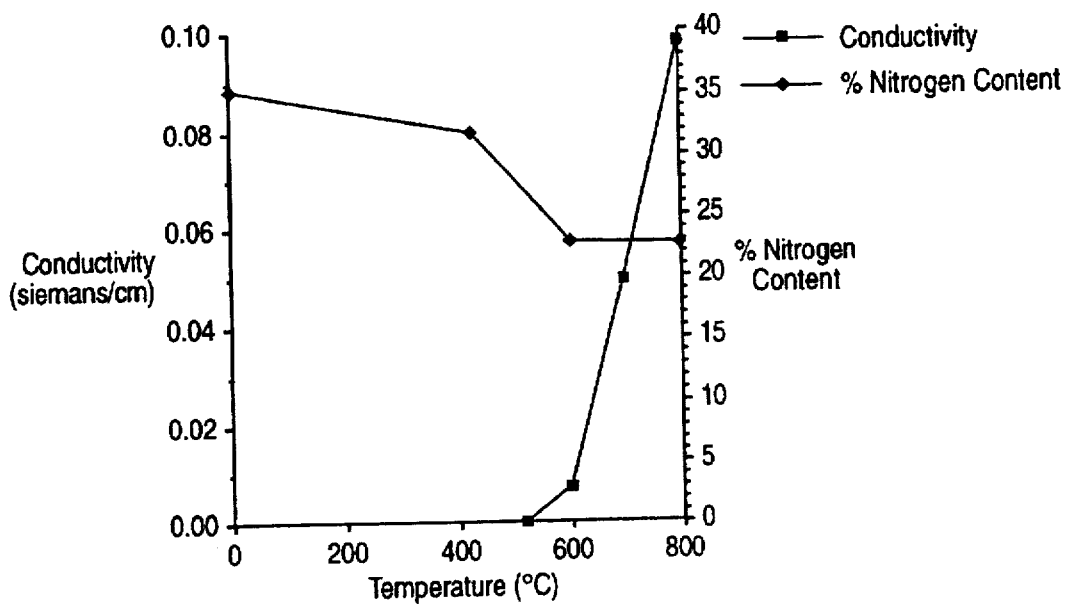
FIG. 6 contains graphs; one showing percent nitrogen content versus temperature for crotodamn and the other plot shows conductivity versus temperature for crotodamn. The temperature is in degree centigrade, the conductivity is in Siemens per centimeter, and the nitrogen content is expressed as percent by weight.
Figure 7:
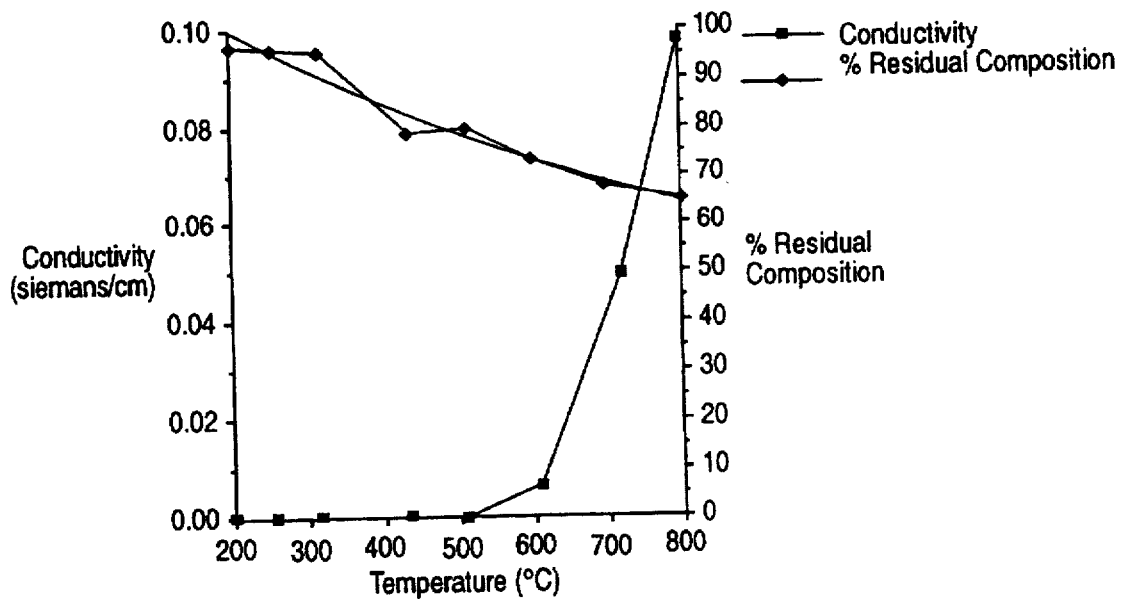
FIG. 7 shows graphs, one of which is a plot of percentage residual composition versus temperature for crotodamn, and the other is a plot of conductivity versus temperature for crotodamn. The temperature and conductivity are expressed in units as described with reference to FIG. 6. The percent residual composition is defined as weight percent remaining sample after thermolysis.
Figure 8:
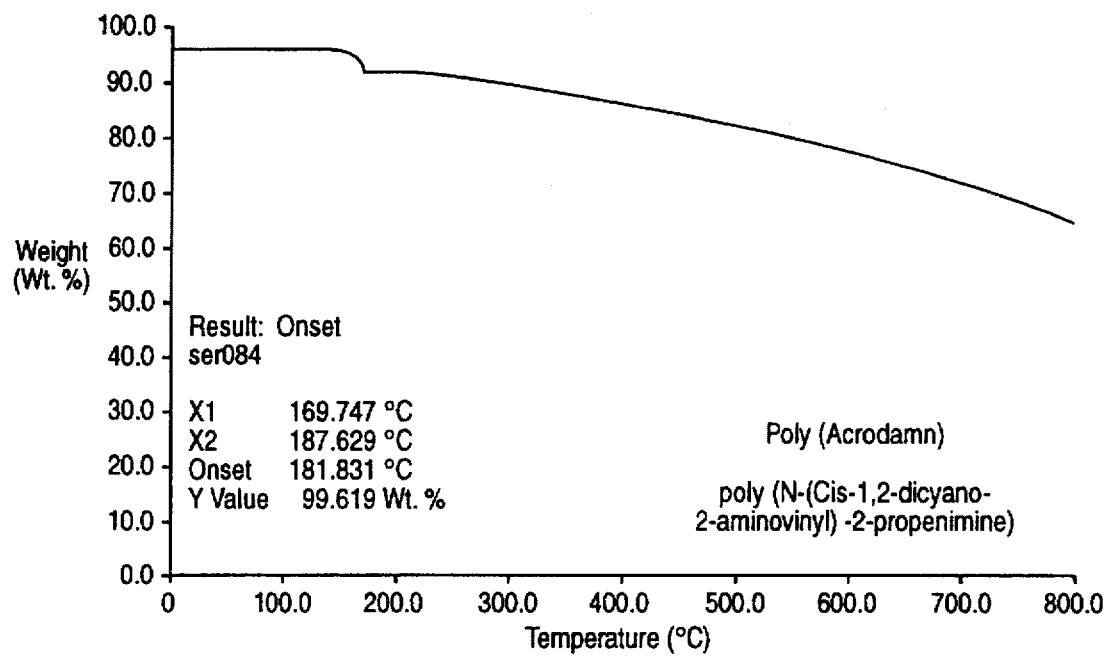
FIG. 8 shows the results of TGA (thermal gravimetric analysis) trace for the acrodamn and the polyacrodamn, starting from the monomer.
Figure 9:
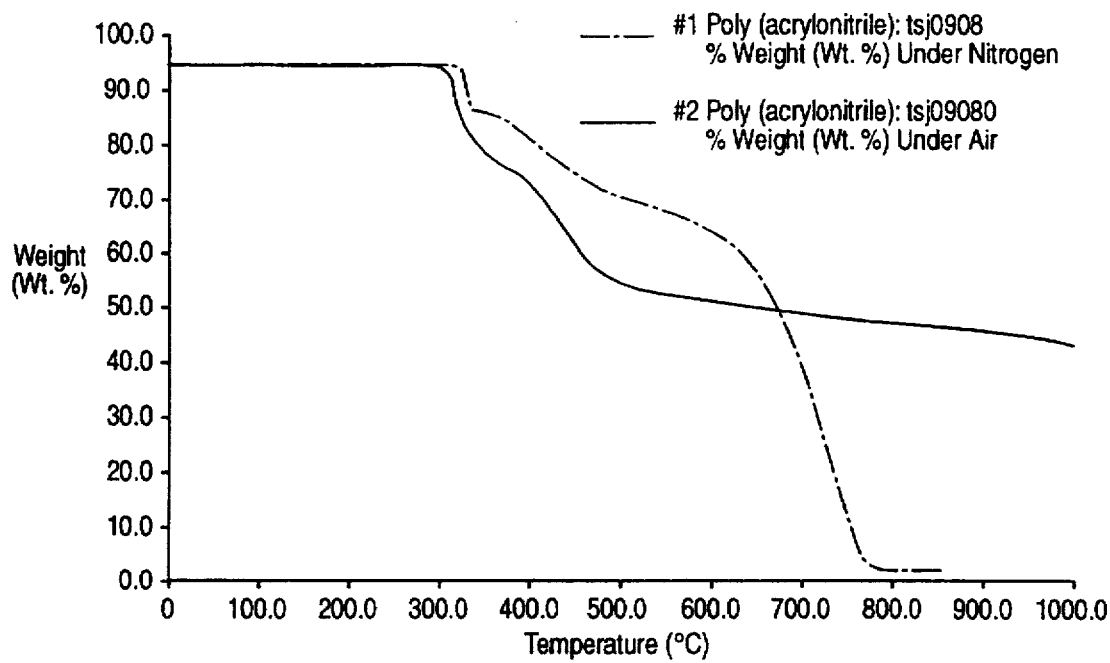
FIG. 9 is a comparative TGA showing analysis for poly (acrylonitrile) (PAN). The solid line is under nitrogen and the dashed line is under air.

Each of the aforesaid compounds N-(cis-1,2-dicyano-2-aminovinyl)-2-butenimine, N-(cis-1,2-dicyano-2-aminovinyl)-2-propenimine, N-(cis-1,2-dicyano-2-aminovinyl)-2-methylpropenimine, and N-(cis-1,2-dicyano-2-ethylaminovinyl)-2-propenimine of Examples I through IV (FIGS. 1 through 3 and 5); and polymers of FIG. 4 were each synthesized. A major feature of the composition of the invention is the thermal stability and the very low level of vaporization with increased temperature. It is noteworthy that thermally stable materials can be generated directly from the monomer. The pyrolysis characteristics of both the monomer and the polymer have been investigated (FIGS. 6, 7, 8 and comparative FIG. 9). In the decomposition reaction very low gas evolution is encountered due to the unusual stoichiometric composition of the monomers and polymers. Eventually, as the temperature is raised, graphitization takes place. Surprisingly, when thermolysis is carried out under nitrogen, well over half the weight of the original monomer is found in the char (carbonaceous material). Accordingly, these materials have potential applications in coatings, flame retardants, and specialty materials which require high oxidation resistant forms of carbon. Very low loss of volatiles occurs throughout a heating cycle for thermal decomposition of the monomers and the polymers up to 800° C. under nitrogen (FIGS. 6, 7, and 8). The products of such thermal decomposition (pyrolysis) are generally graphitic in nature but contain, by elemental analysis, an unusually high percentage of residual nitrogen. The TGA (thermal gravimetric analysis) traces, (FIG. 8), is for the acrodamn monomer and polymers which melt polymerize and then decomposes as the temperature increases. FIG. 9 is a comparative TGA of polyacrylonitrile. The TGA, carried out under nitrogen gas for acrodamn (FIG. 8), is quite remarkable for an organic material. The remaining mass at 80° C. is 70 percent of the starting monomer. By comparison the TGA for poly (acrylonitrile) (PAN) is shown. PAN fiber is commercially used as a precursor to high strength carbon fiber. Any loss of weight during thermolysis (pyrolysis) represents lowering of the yield. It can be seen from the comparative TGA (FIG. 9) that PAN gives a lower carbon yield (50 percent) than polyacrodamn starting from the monomer. Presently, melamine, with its high nitrogen content, is used commercially as a non-halogen flame retardant. Although it is considered thermally quite robust, its TGA shows the pattern of weight loss one would expect for a molecular species, onset of rapid weight loss at around 300° C. and very low char yield. The TGA analysis of PAN and melamine are in striking contrast to that of the acrodamn monomer which is relatively thermally stable and provides a high carbon char yield.

Returning to FIG. 6, the results of an isothermal thermolysis analysis are quite striking. In this analysis, samples were held at the test temperature for 24 hours in a tube furnace under nitrogen. Following this, the samples were analyzed for carbon, hydrogen, and nitrogen, and for oxygen by difference. The results are shown in FIG. 6. Several features are noteworthy. Although it was clear that the low weight loss could only imply retention of considerable nitrogen, the starting nitrogen content was 35 percent, for example, for crotodamn. It is surprising to find that after presumed graphitization at 800° C., the nitrogen content is still 23 percent. This implies the formation of a novel structure with an atomic ratio of carbon to nitrogen similar to that of pyridine. Furthermore, although graphitization, as assayed by conductivity, occurs in the vicinity of 700° C., there was not observed any particular weight loss accompanying what is presumably a major structural transition. The very low loss of volatiles suggests that these new compounds are well adaptable for applications involving flame retardation. The conductivity increases dramatically between 600° C. and 800° C., reaching about 0.10 Siemens per centimeter.

Figure 27:
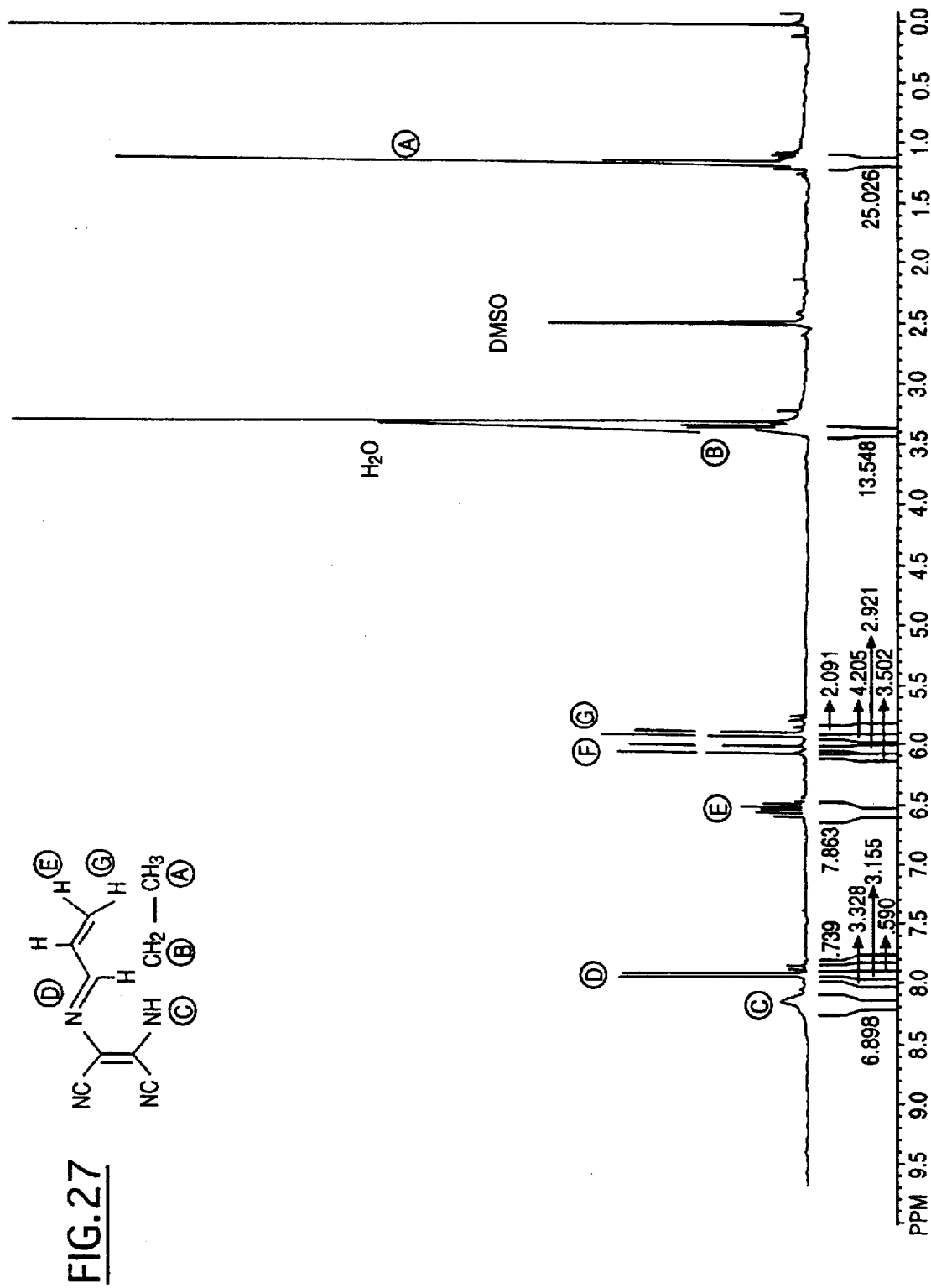
FIG. 27 is a $^{proton}$H type NMR of N-(cis-1,2-dicyano-2-ethylaminovinyl)-2-propenimine (N-Ethylacrodamn of FIG. 28).
Figure 28:
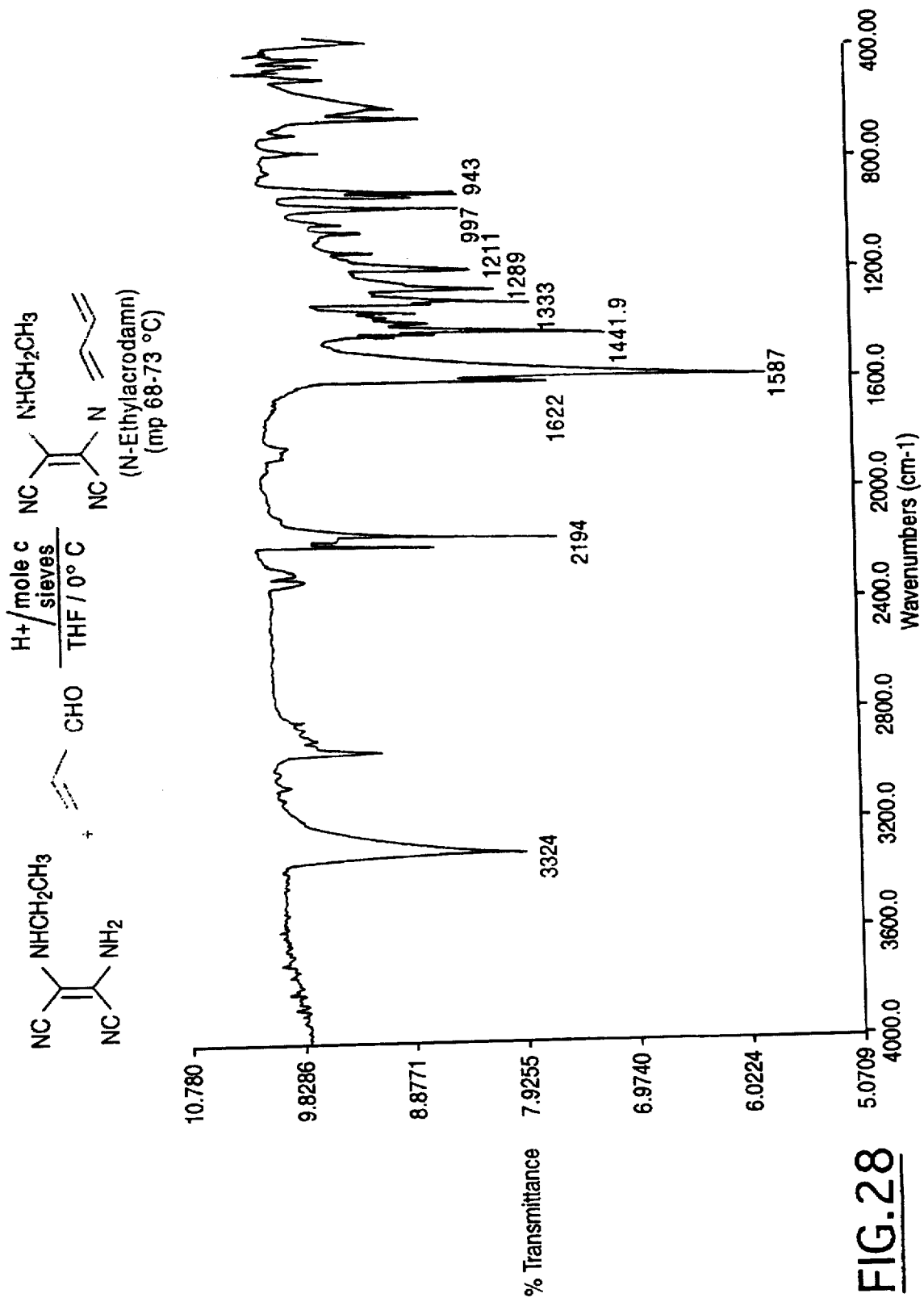
FIG. 28 is a KBr pellet type IR spectra of N-(cis-1,2-dicyano-2-ethylaminovinyl)-2-propenimine (N-Ethylacrodamn).

FIGS. 10 through 15 all pertain to the crotodamn of FIG. 3. FIGS. 16 through 21 all pertain to the acrodamn of FIG. 1. FIGS. 22 through 26 all pertain to the methacrodamn of FIG. 2. FIGS. 27 and 28 all pertain to the N-Ethylacrodamn.

Figure 10:
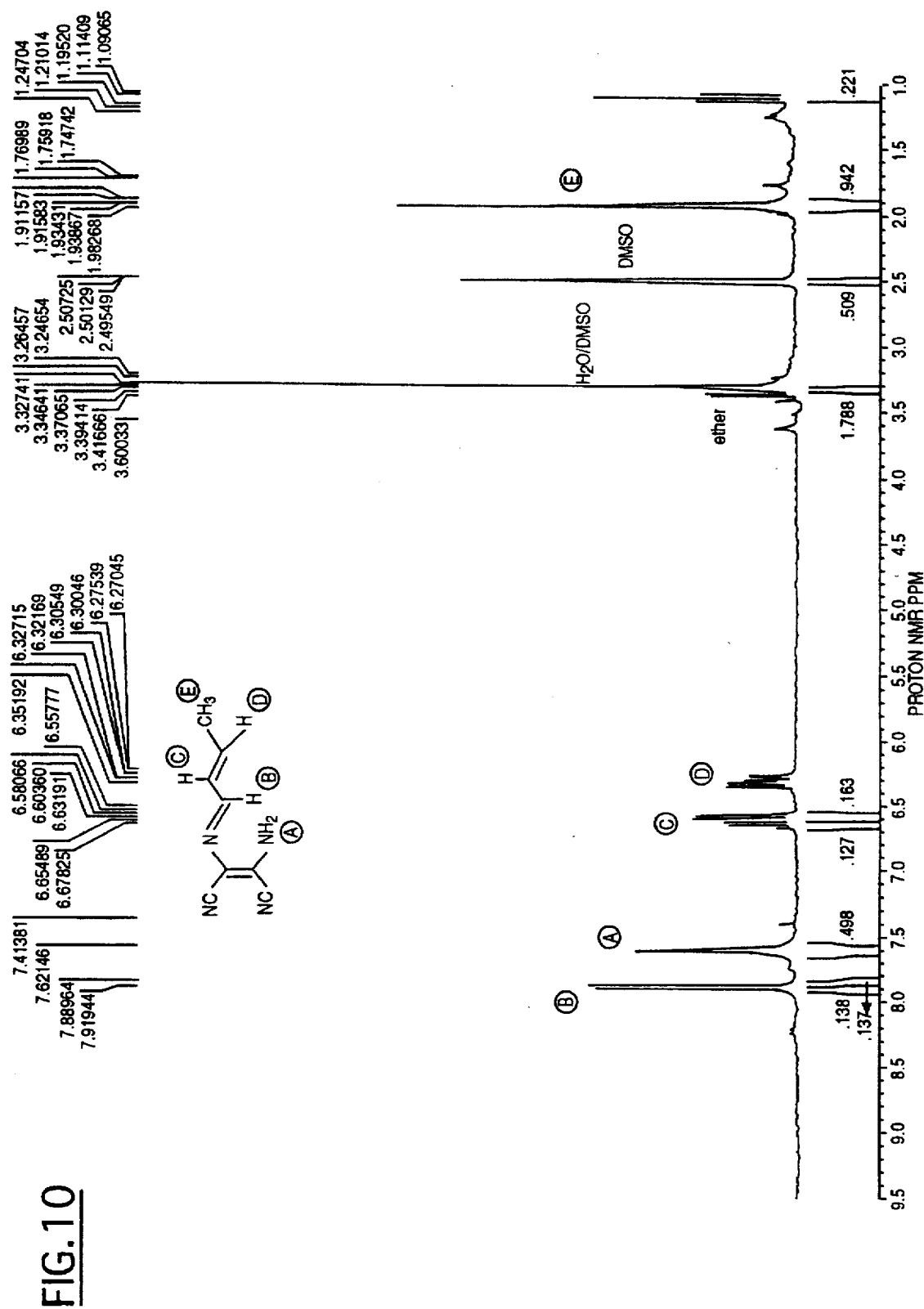
FIG. 10 is a $^{proton}$H type NMR of N-(cis-1,2-dicyano-2-aminovinyl)-2-butenimine (crotodamn of FIG. 3).
Figure 11:
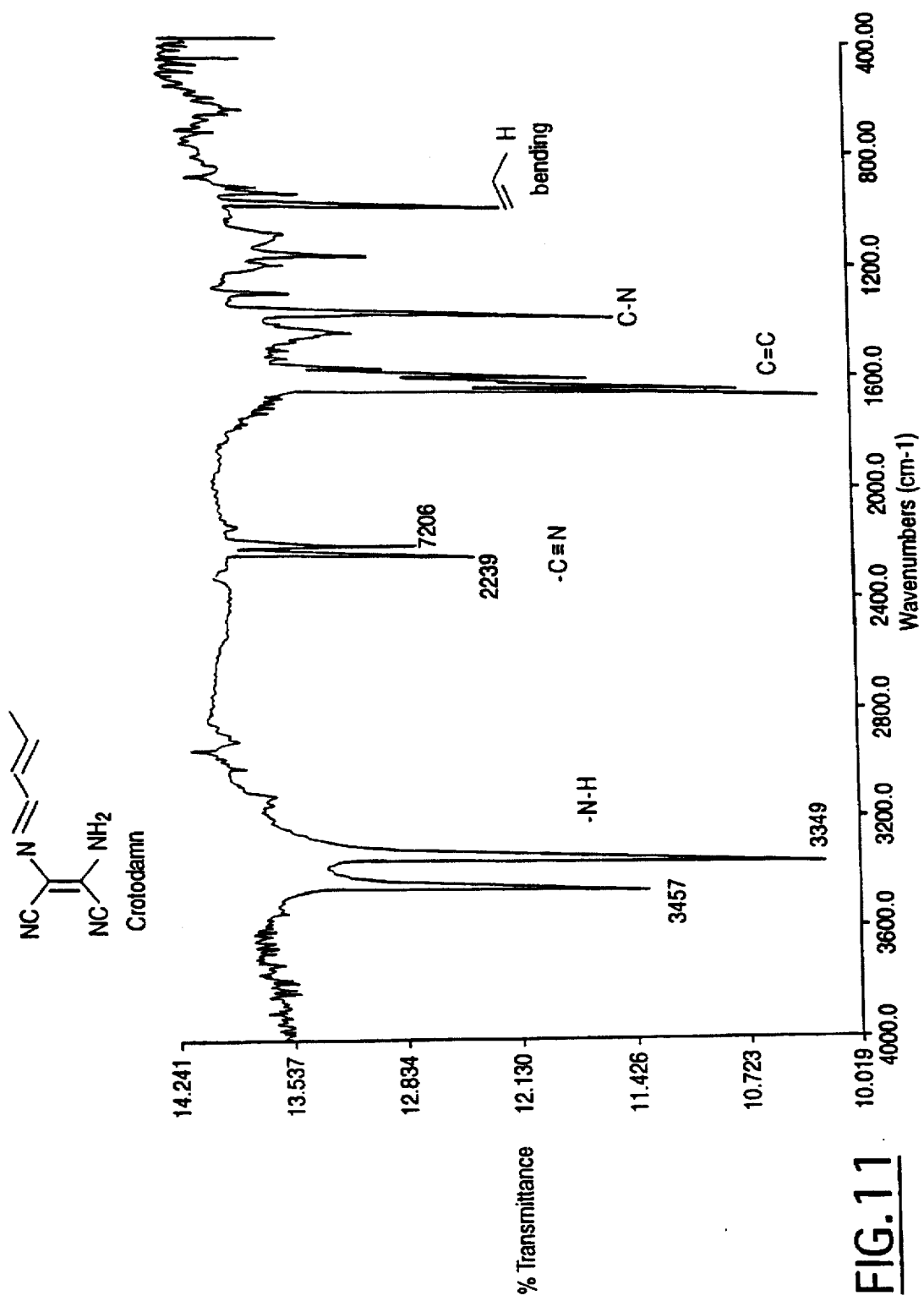
FIG. 11 is a KBr type IR spectra of N-(cis-1,2-dicyano-2-ethylaminovinyl.)-2-butenimine (crotodamn).
Figure 12:
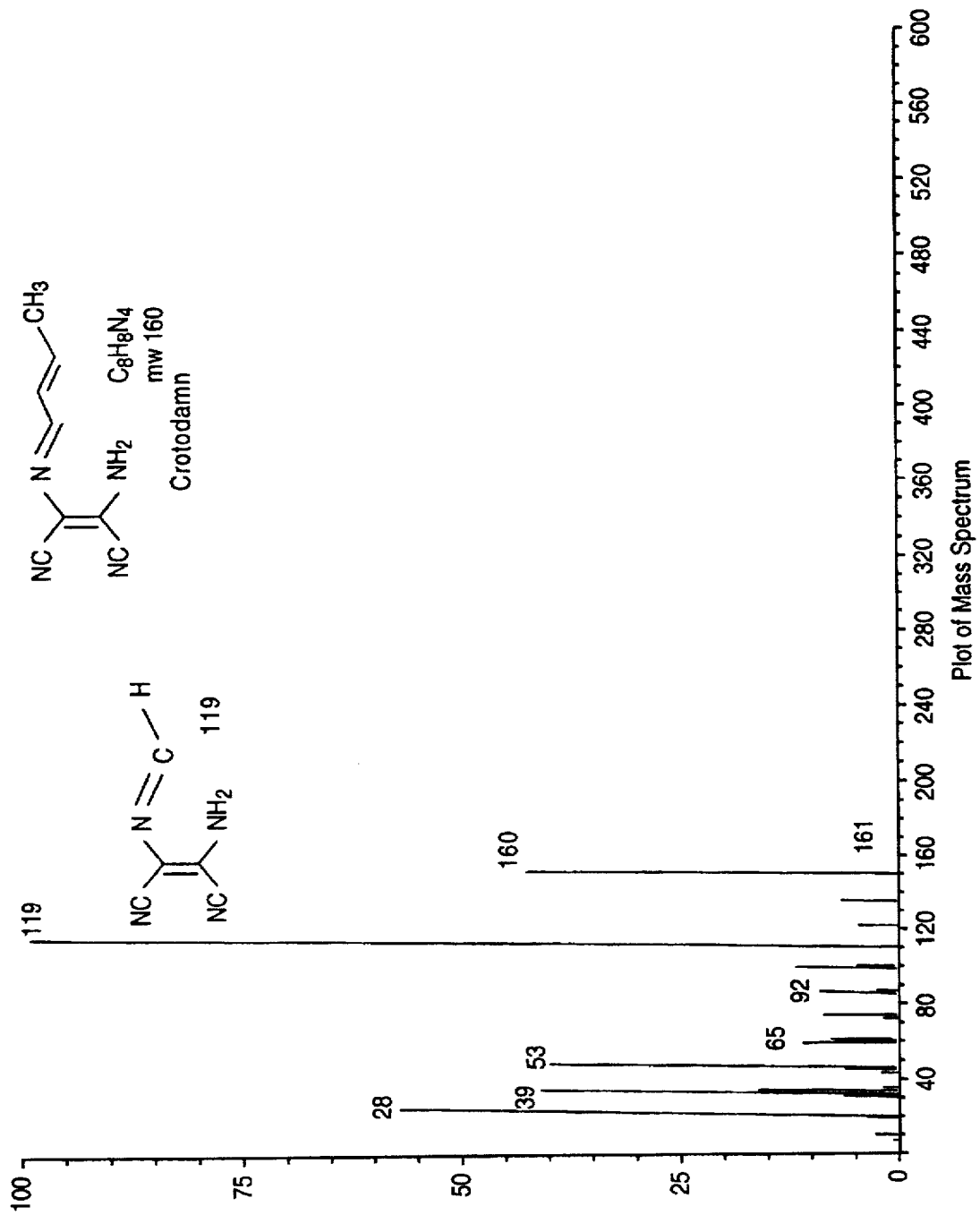
FIG. 12 is a mass spectrum of N-(cis-1,2-dicyano-2-ethylaminovinyl)-2-butenimine (crotodamn).
Figure 16:
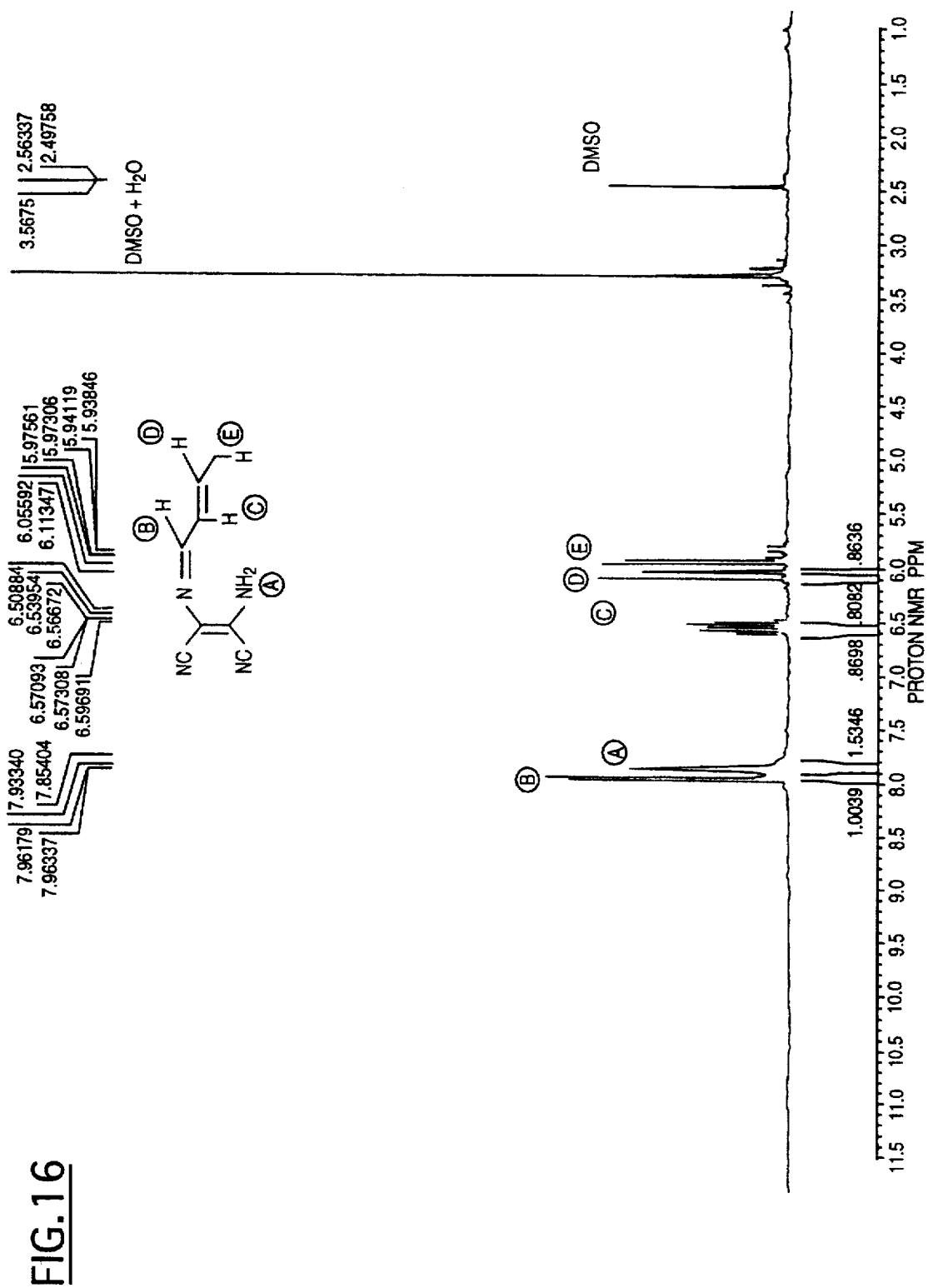
FIG. 16 is a $^{proton}$H type NMR of N-(cis-1,2-dicyano-2-aminovinyl-2-propenimine (acrodamn of FIG. 1).
Figure 17:
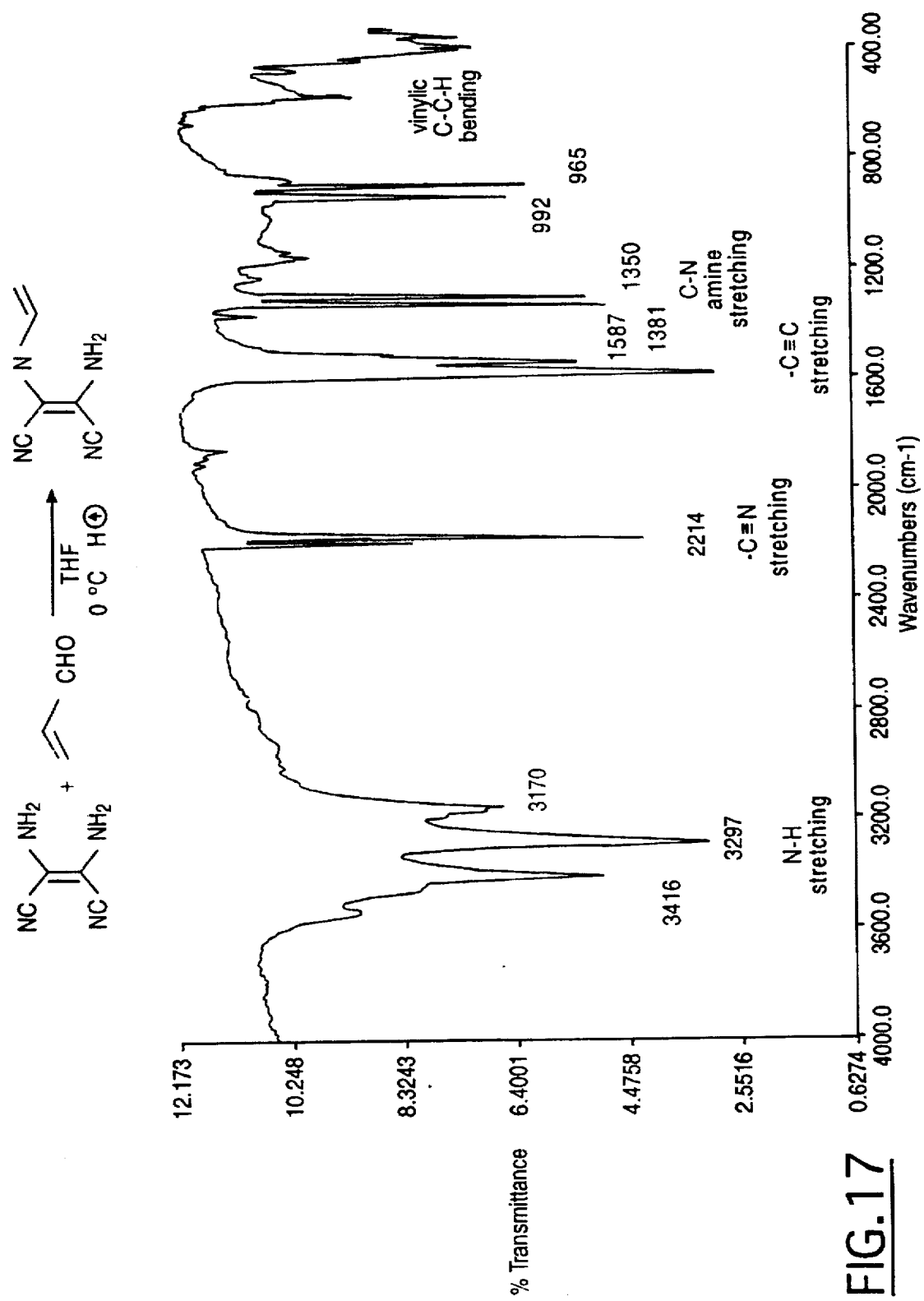
FIG. 17 is a KBr type IR spectra of N-(cis-1,2-dicyano-2-aminovinyl)-2-propenimine (acrodamn).
Figure 18:
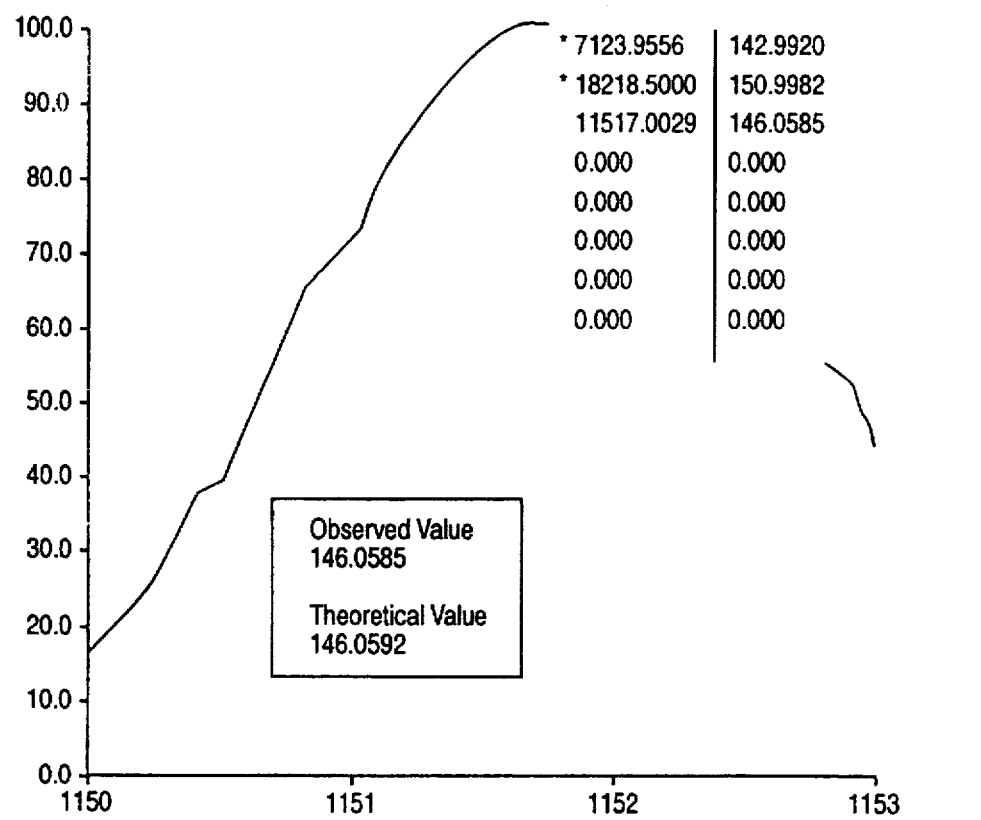
FIGS. 18 and 19 are respectively accurate mass spectrum calculation and fingerprint regular resolution spectrum of N-(cis-1,2-dicyano-2-aminovinyl)-2-propenimine (acrodamn).
Figure 19:
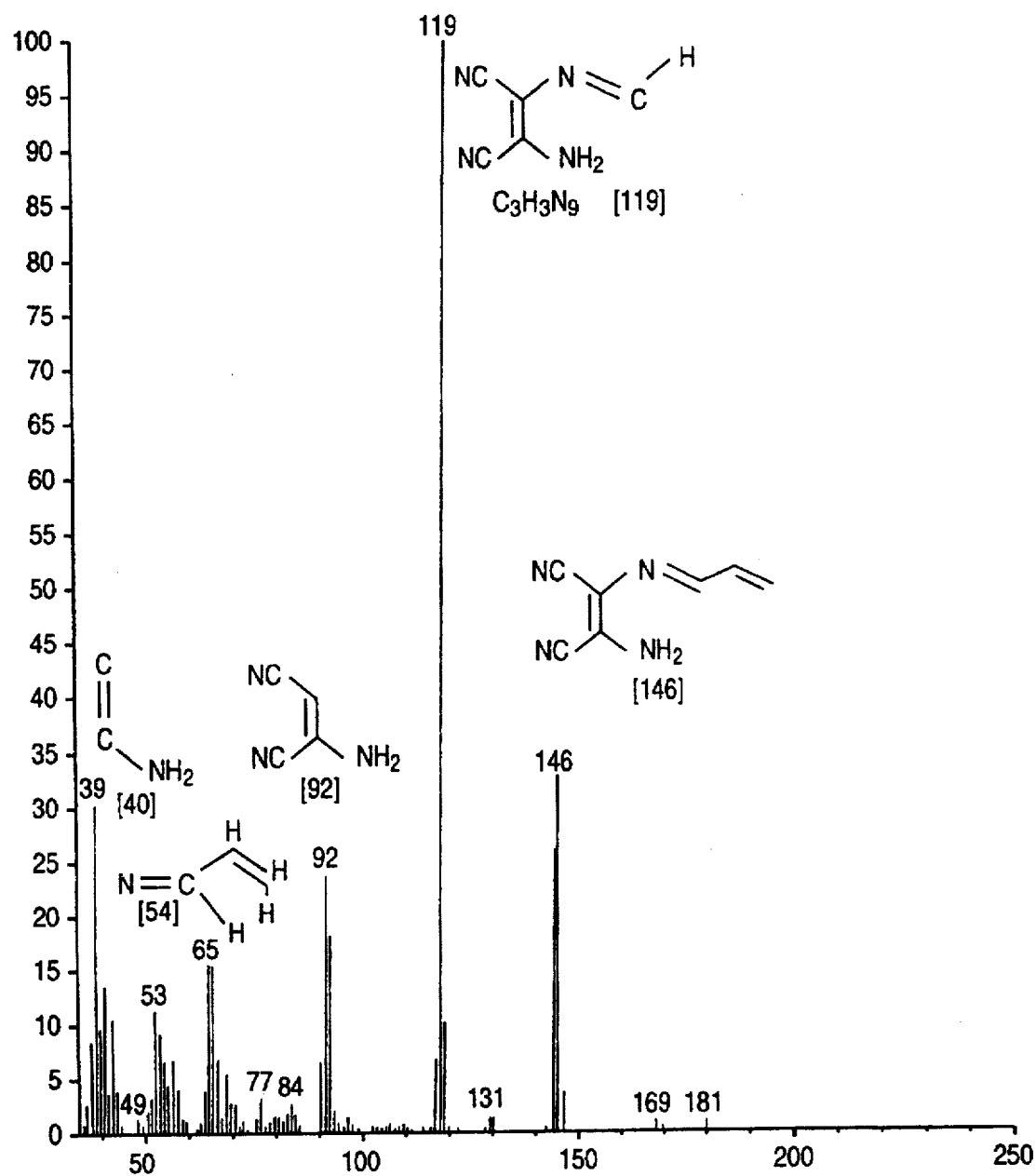
Figure 22:
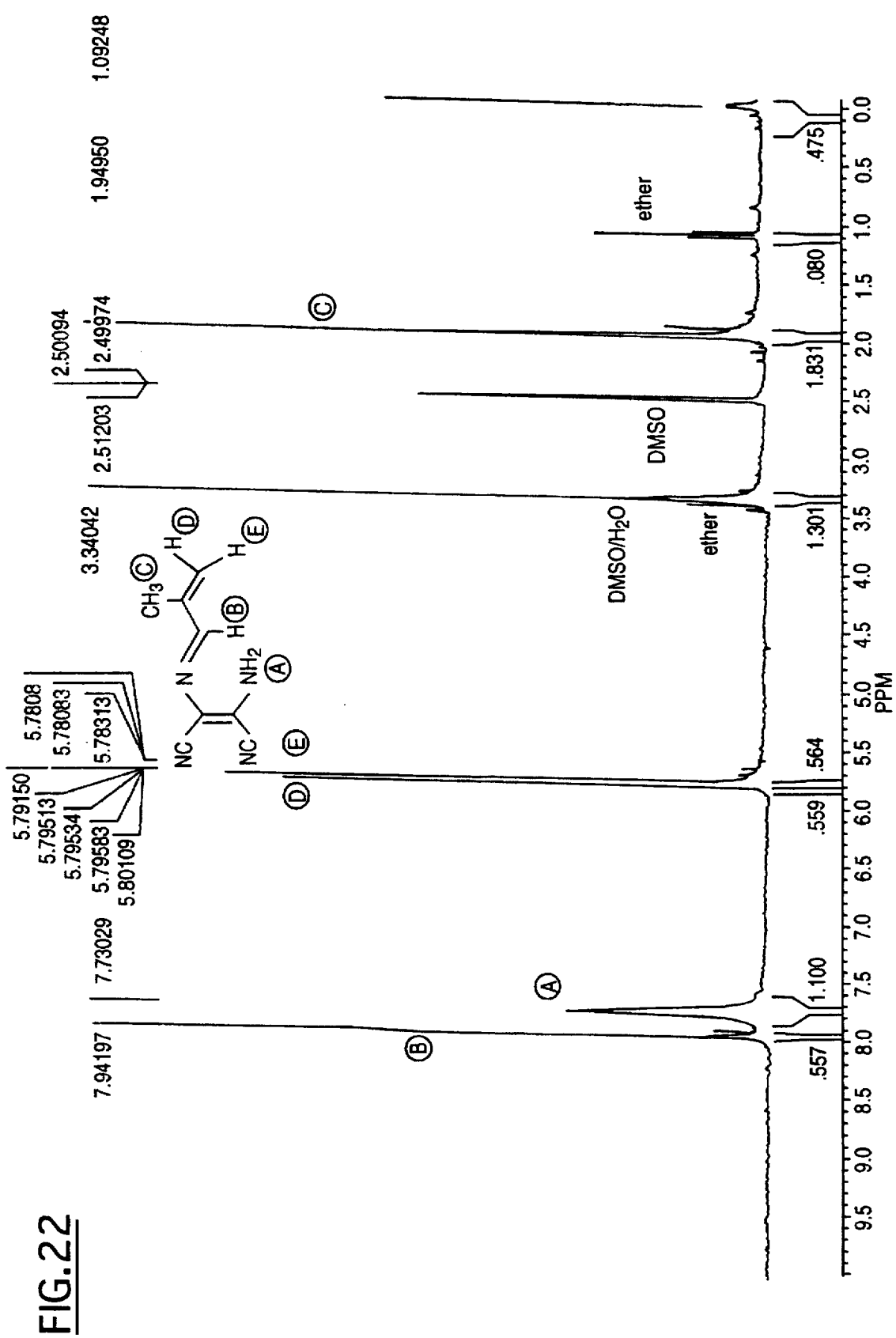
FIG. 22 is a $^{proton}$H type NMR of N-(cis-1,2-dicyano-2-aminovinyl)-2-methylpropenimine (methacrodamn of FIG. 2).
Figure 23:
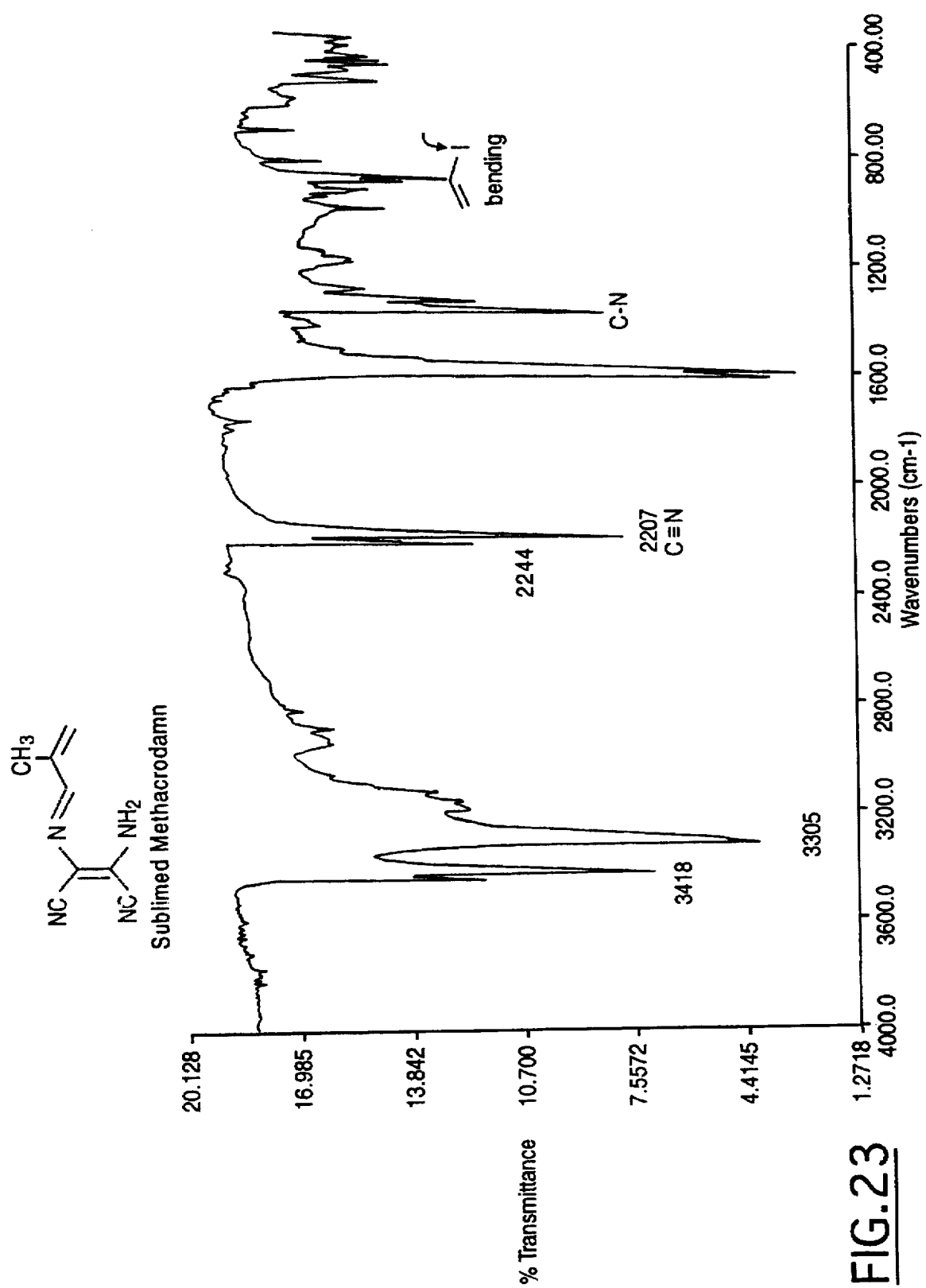
FIG. 23 is a KBr type IR spectra of N-(cis-1,2-dicyano-2-aminovinyl) -2-methylpropenimine (methacrodamn).
Figure 24:
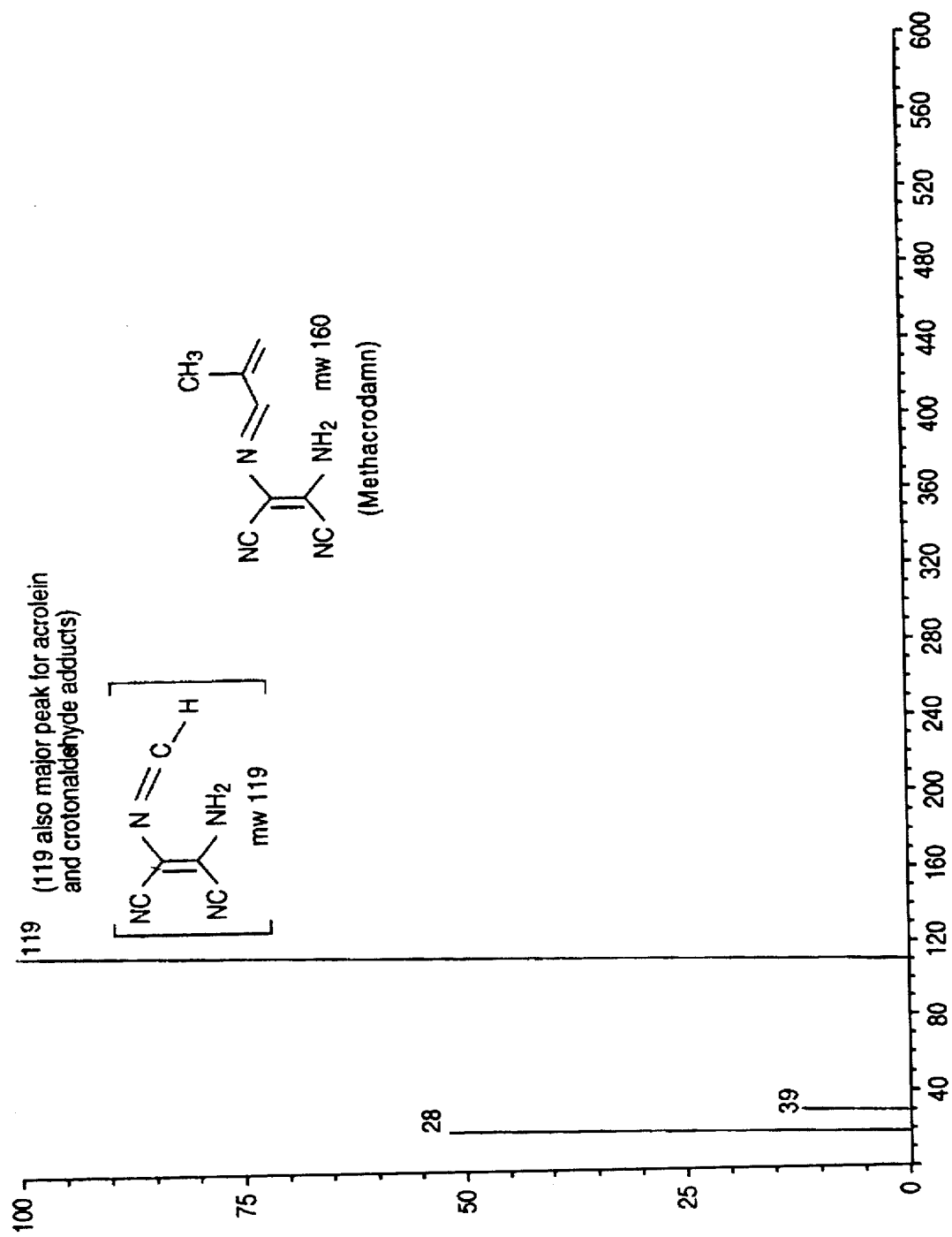
FIG. 24 is a mass spectrum of N-(cis-1,2-dicyano-2-aminovinyl)-2-methylpropenimine (methacrodamn).

FIGS. 10, 16, and 22 are proton NMR spectrum of respectively crotodamn, acrodamn, and methacrodamn, each of the proton NMR spectrum show the. The hydrogen in the respective molecules are marked by designations, such as A, B, C, D, and E, and the spectral absorptions assigned to those respective hydrogens are indicated. FIGS. 11, 17, and 18 are infrared spectrum of respectively crotodamn, acrodamn, and methacrodamn. FIGS. 11, 17, and 23 contain indications of the bonds being shown by the respective peaks. FIGS. 12, 18, 19, and 24 are mass spectrum. FIG. 12 is a mass spectrum of crotodamn; FIG. 18 and 19 are respectively mass spectral data for acrodamn and regular resolution mass spectrum for acrodamn; and FIG. 24 is mass spectrum of methacrodamn. In each of these cases, the respective signals indicate the presence of the structures for the compounds of the invention.

Figure 13:
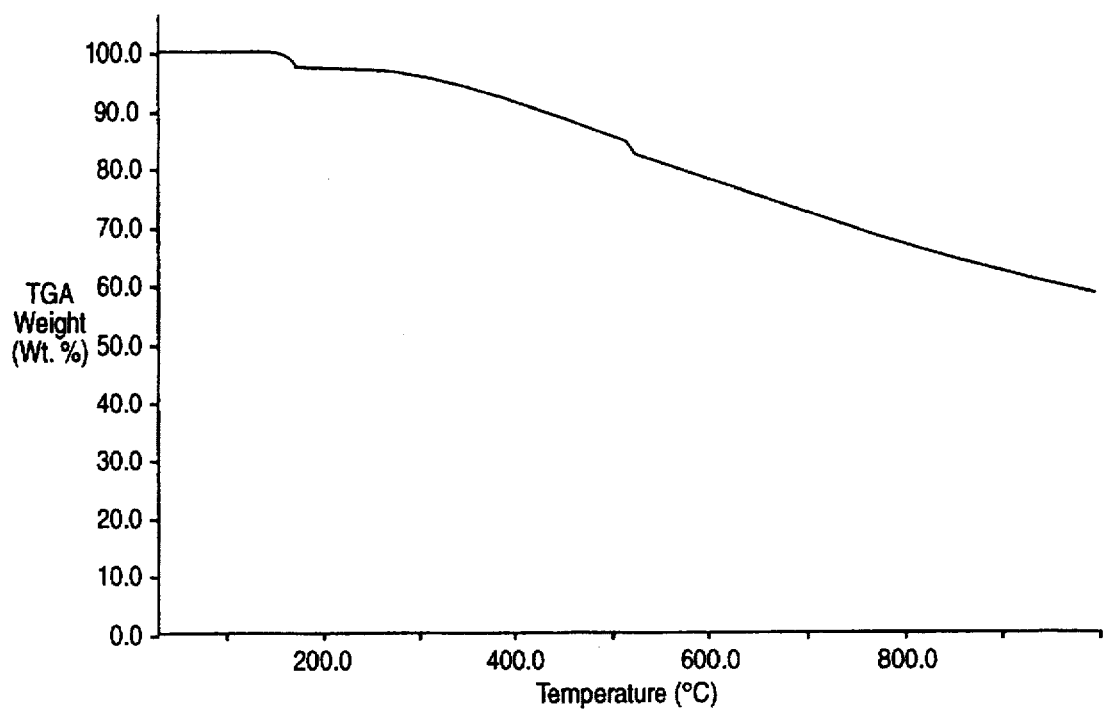
FIGS. 13 and 14 are graphs showing the results, of TGA (thermal gravimetric analysis) of N- (cis-1,2-dicyano-2-ethylaminovinyl)-2-butenimine (crotodamn).
Figure 14:
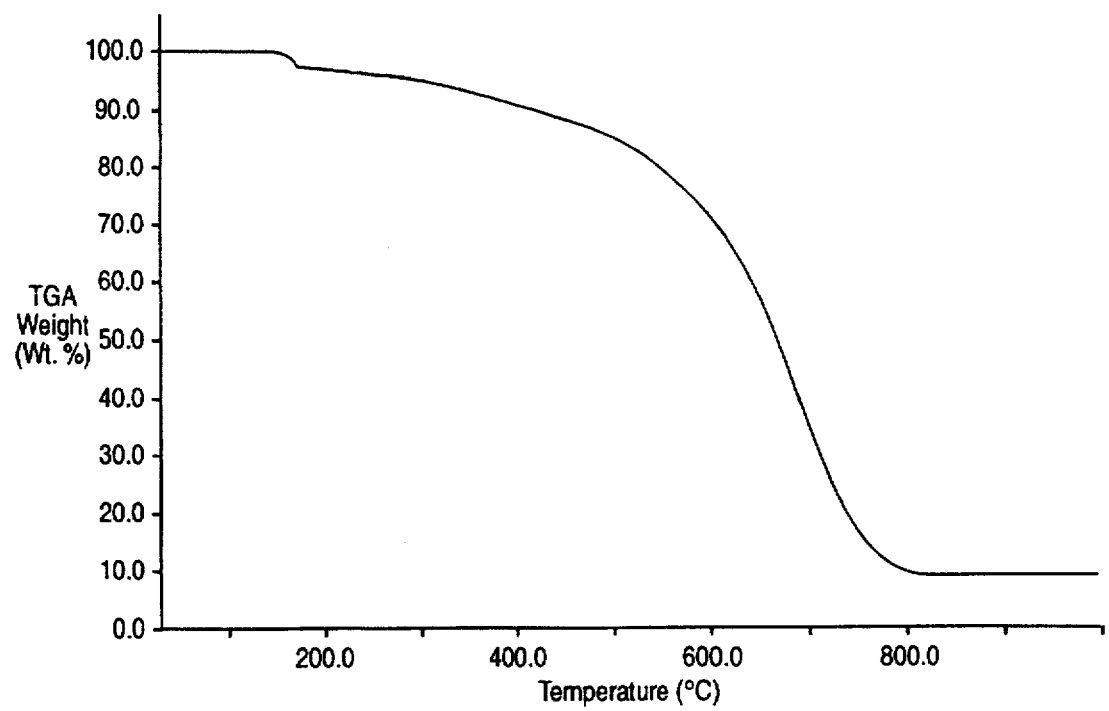
Figure 20:
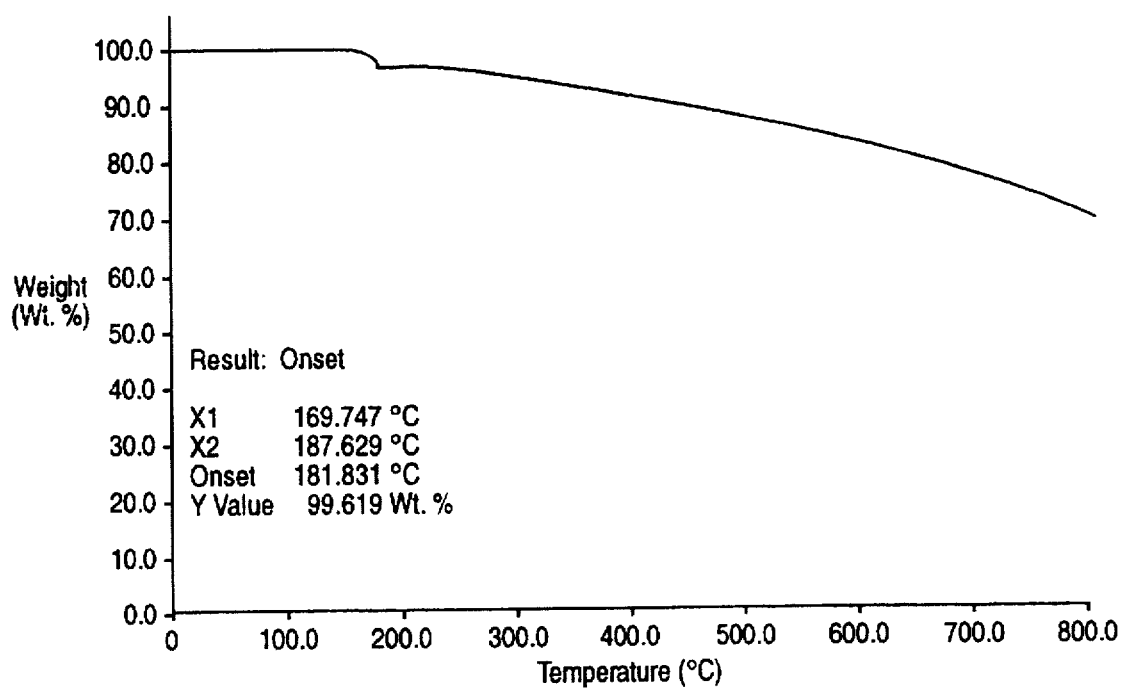
FIG. 20 is a graph showing the results of TGA (thermal gravimetric analysis) of N-(cis-1,2-dicyano-2-aminovinyl)-2-propenimine (acrodamn).
Figure 25:
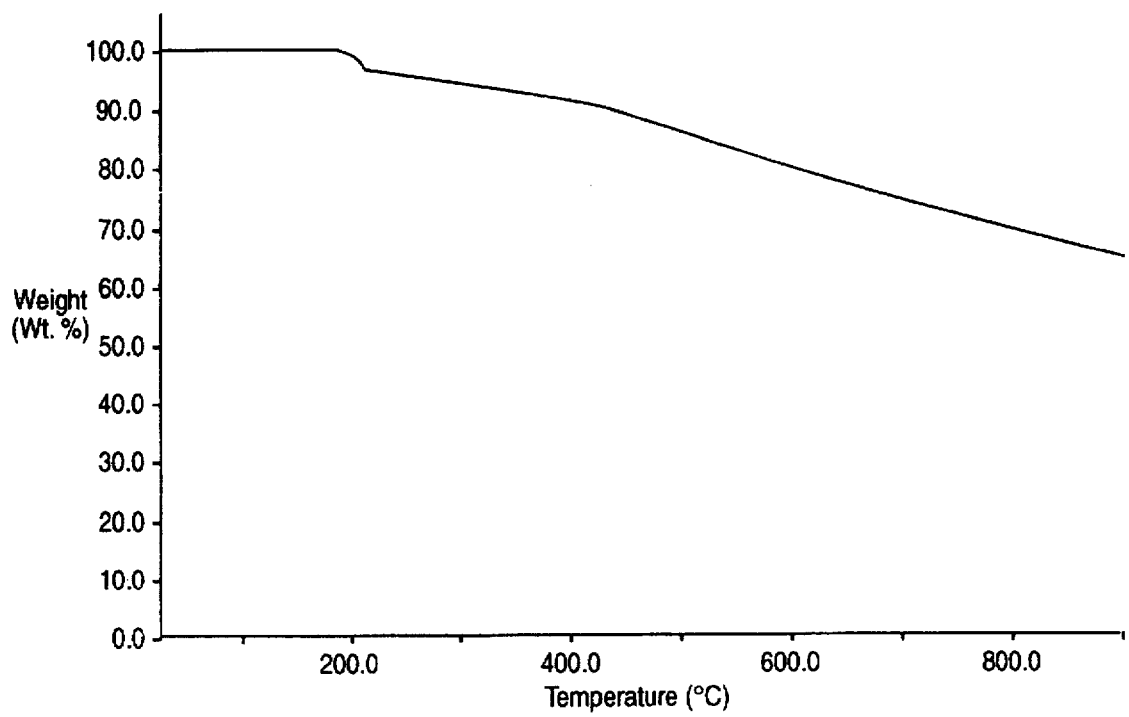
FIG. 25 is a graph showing the results of TGA (thermal gravimetric analysis) of N-(cis-1,2-dicyano-2-aminovinyl)-2-methylpropenimine (methacrodamn).

FIGS. 13, 14, 20, and 25 are thermal gravimetric analyses. FIG. 13 shows TGA of crotodamn under nitrogen and FIG. 14 shows TGA of crotodamn under air. FIG. 20 shows TGA for acrodamn and FIG. 25 shows TGA for methacrodamn. FIGS. 13, 14, 20, and 25 as discussed in connection with FIGS. 6 through 9, TGA analysis shows the thermal stability of the monomers. The contour of the TGA curves is consistent with the differential scanning calorimeter curves (calorigrams) where melting and polymerization occur.

Figure 15:
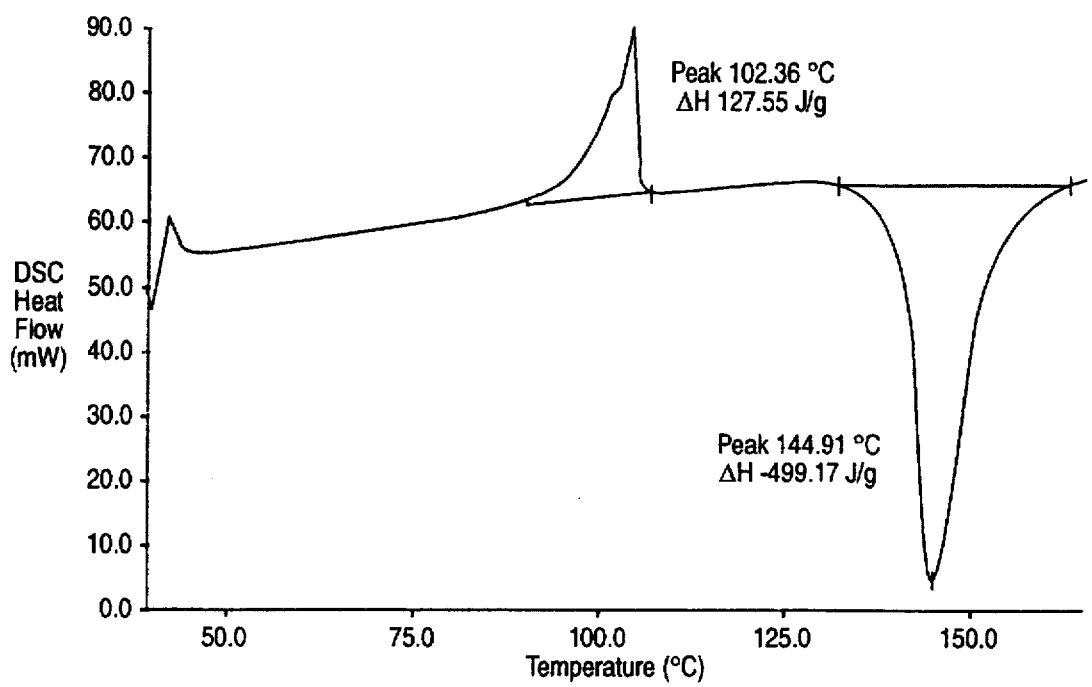
FIG. 15 shows the results of DSC (differential scanning calorimeter) analysis of an N-(cis-1,2-dicyano-2-ethylaminovinyl)-2-butenimine (crotodamn).
Figure 21:
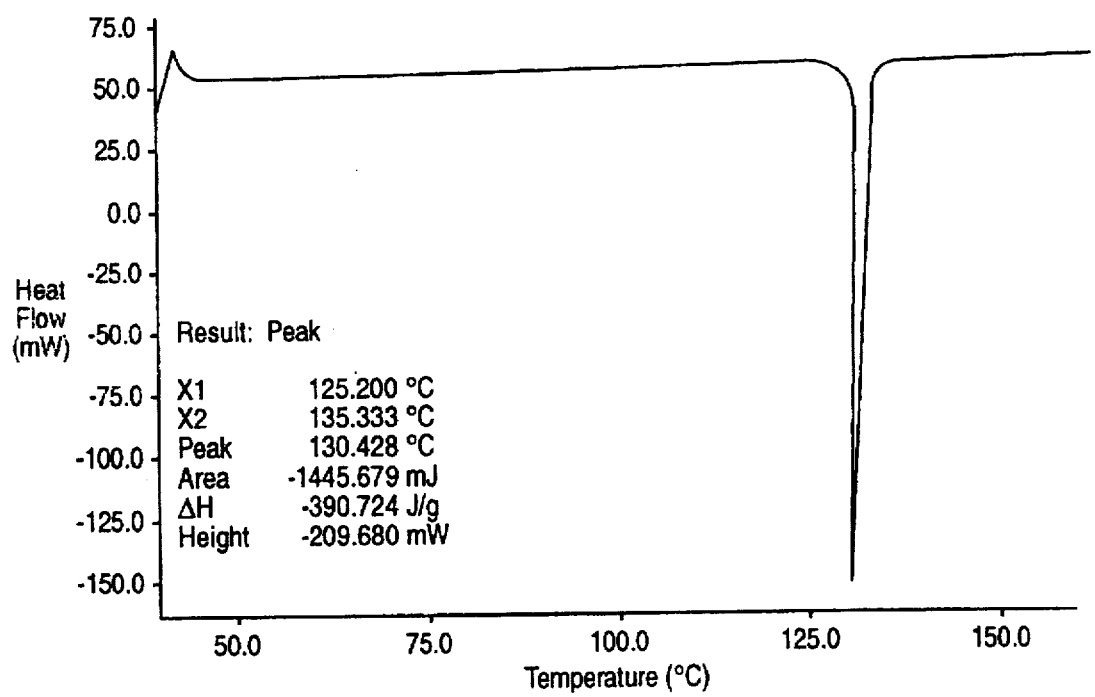
FIG. 21 shows the results of DSC (differential scanning calorimeter) analysis of an N-(cis-1,2-dicyano-2-aminovinyl)-2-propenimine (acrodamn).
Figure 26:
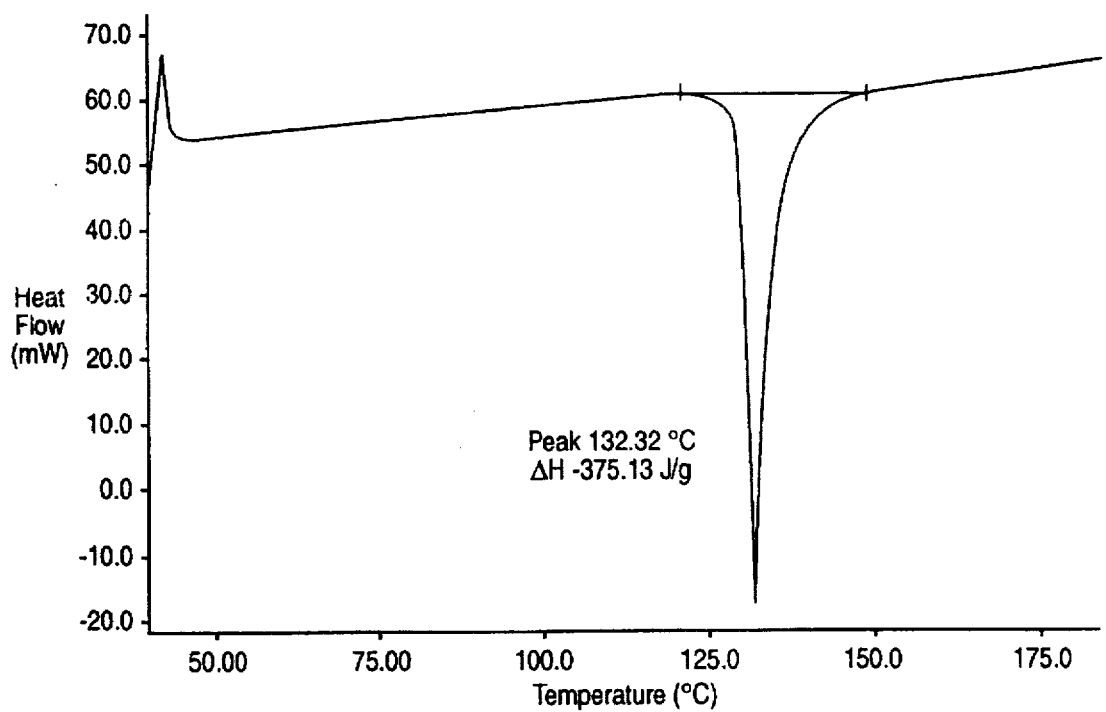
FIG. 26 shows the results of DSC (differential scanning calorimeter) analysis of an N-(cis-1,2-dicyano-2-aminovinyl)-2-methylpropenimine (methacrodamn).

FIGS. 15, 21, and 26 show differential scanning calorigrams (DSC) of respectively crotodamn, acrodamn, and methacrodamn. In FIG. 15 the endothermic peak at 102° C. is melting. The exothermic peak at 145° C. indicates polymerization. In FIG. 21 the exotherm at 130° C. is due to polymerization. In FIG. 26 the exotherm at 132° C. is due to polymerization.

FIGS. 27 and 28 respectively shown proton NMR spectrum and infrared spectrum for N-ethylacrodamn, monomeric precursor for forming linear polymer. In FIG. 27 the spectral absorptions labelled A through G are consistent with the presence of the hydrogens at their respective locations A through G in a molecule shown above the chart. The infrared spectrum of FIG. 28 is consistent with the proton NMR of FIG. 27.

Figure 29:
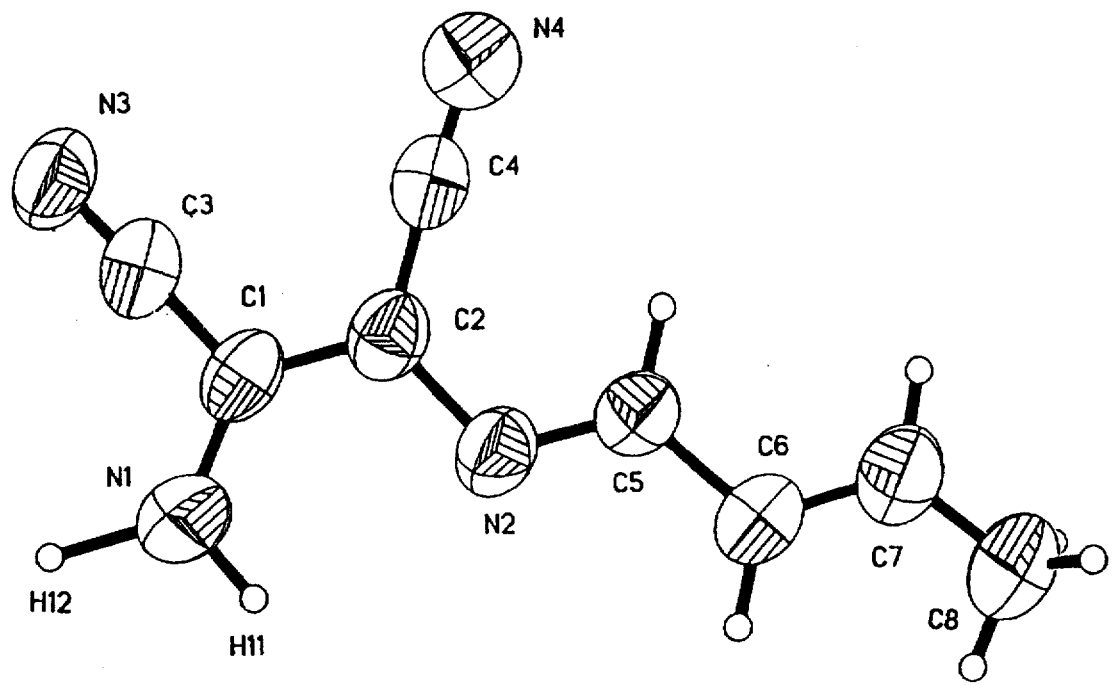
FIG. 29 shows a perspective drawing of the solid-state structure for $C_8H_8N_4$ (crotodamn) with all nonhydrogen atoms represented by thermal vibration ellipsoids drawn to encompass 50 percent of their electron density. Hydrogen atoms are represented by arbitrarily-small spheres which are in no way representative of their true thermal motion.
Figure 30:
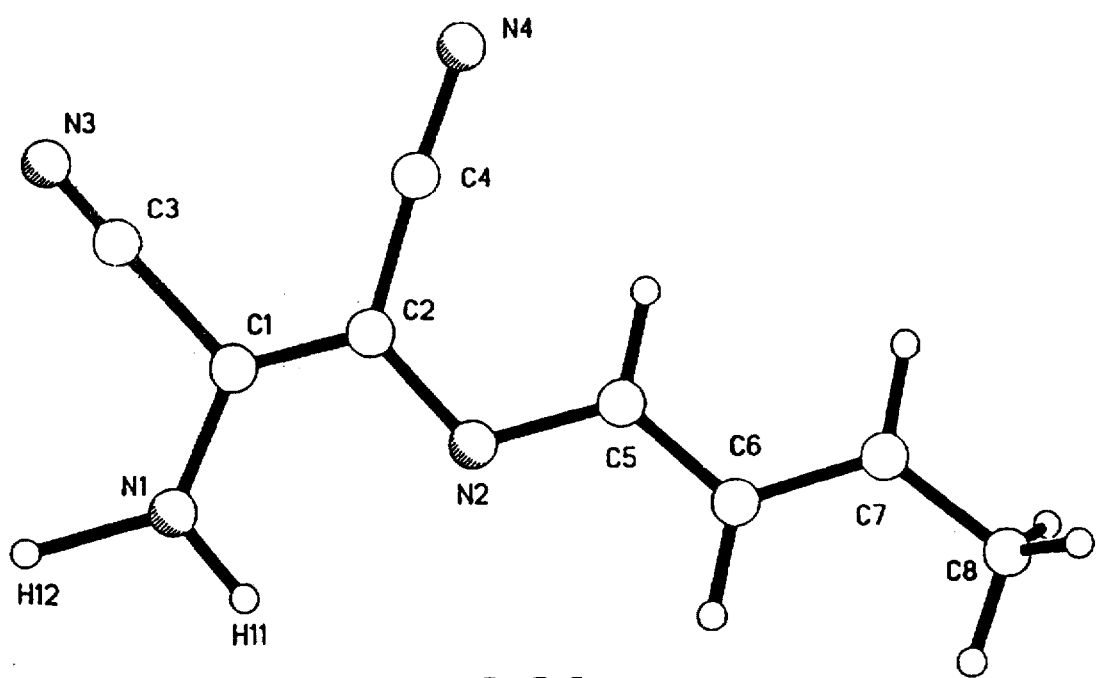
FIG. 30 shows a perspective drawing of the solid state structure for $C_8H_8N_4$ with the nitrogen atoms represented by medium sized shaded spheres and carbon and hydrogen atoms represented by medium sized and small open spheres, respectively.
Figure 31:
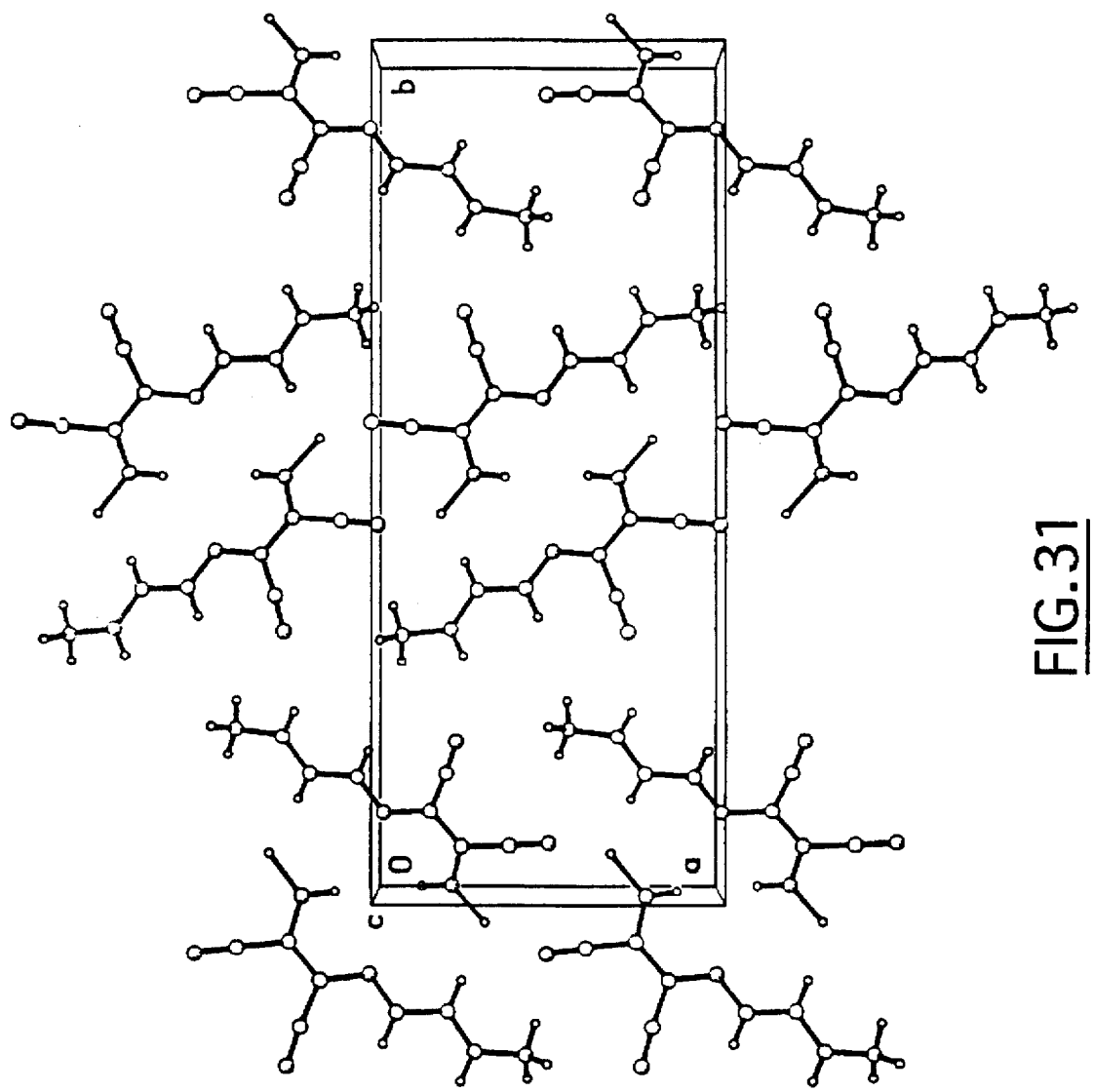
FIG. 31 shows a packing diagram of the solid state structure for $C_8H_8N_4$ viewed down the c axis with atoms represented as shown in FIG. 30.
Figure 32:
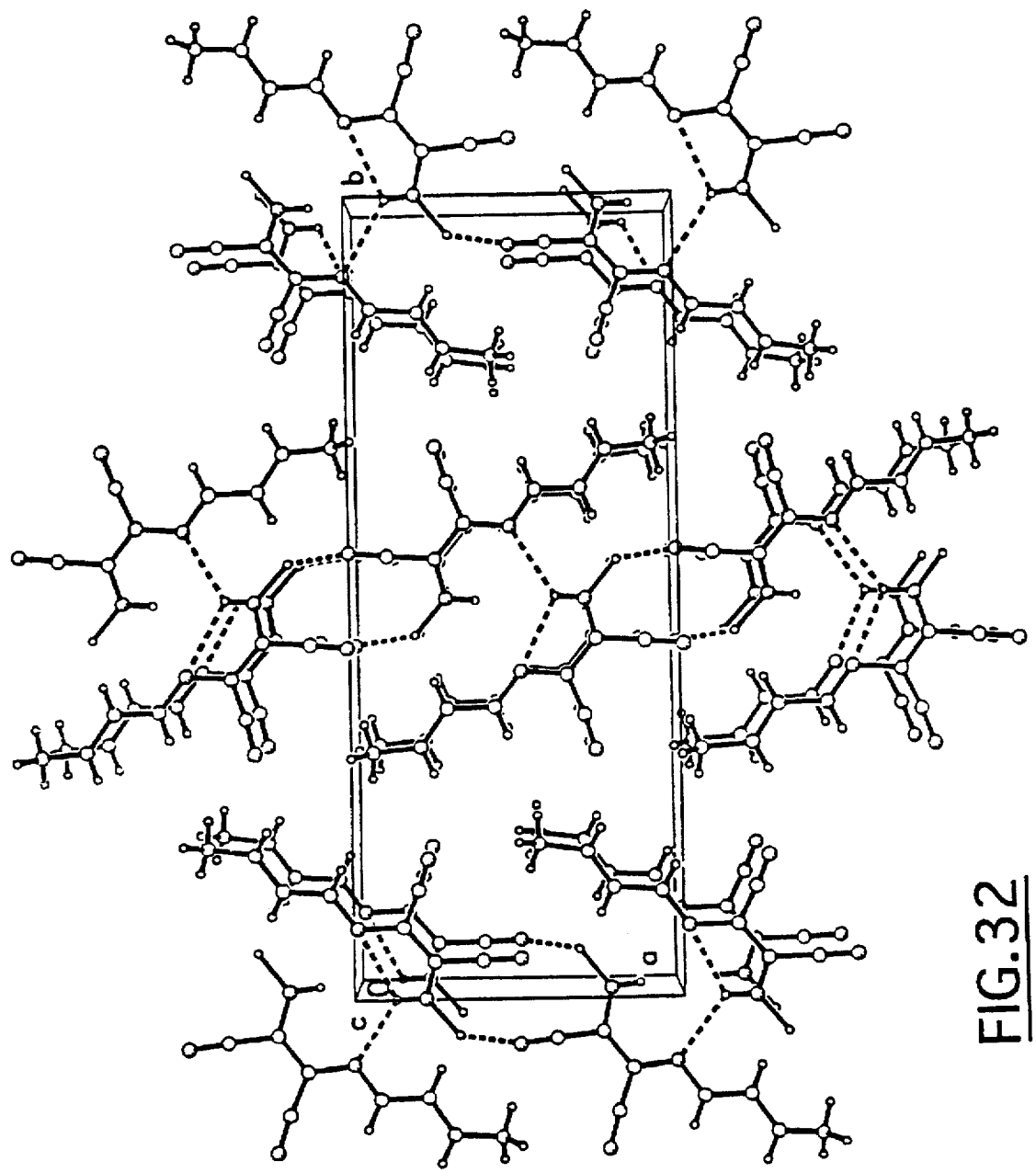
FIG. 32 shows a packing diagram of the solid state structure for $C_8H_8N_4$ viewed down the c axis with atoms represented as shown in FIG. 30. Hydrogen bonding interactions involving $H_{11}$ and $H_{12}$ with $N_2$ and $N_3$, respectively, are shown with dashed lines.
Figure 33:
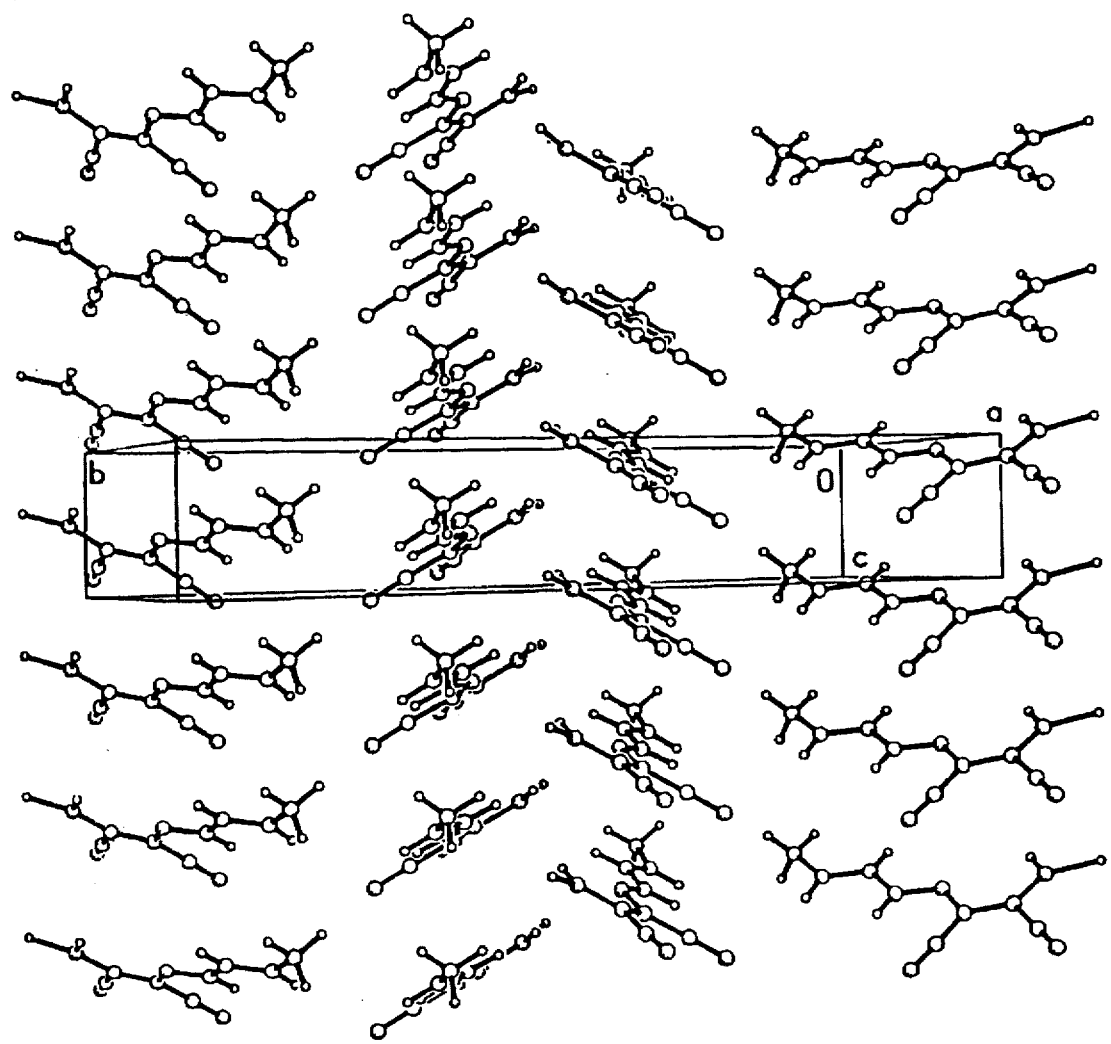
FIG. 33 shows a packing diagram of the solid state structure for $C_8H_8N_4$ viewed perpendicular to the (110) plane with atoms represented as shown in FIG. 30.

The methacrodamn and crotodamn were further characterized by crystal structure analysis. FIGS. 29 and 30 each show a perspective drawing of the solid state structure for $C_8H_8N_4$, crotodamn. FIGS. 31, 32, and 33 each show packing diagrams for the solid state structure as shown in FIG. 30. The crotodamn was yellow in appearance and the crystal structure for this compound of the formula $C_8H_8N_4$ was regular parallelepiped. The lattice constance in the A, B, and C direction in angstroms were respectively 9.423, 23.151, and 3.954. The alpha, beta, and gamma angles were each 90°. The calculated density was 1.233 grams per cubic centimeter. Values were obtained using CuKα radiation with a nickel filter with the scan between two theta settings according to conventional practice.

Figure 34:
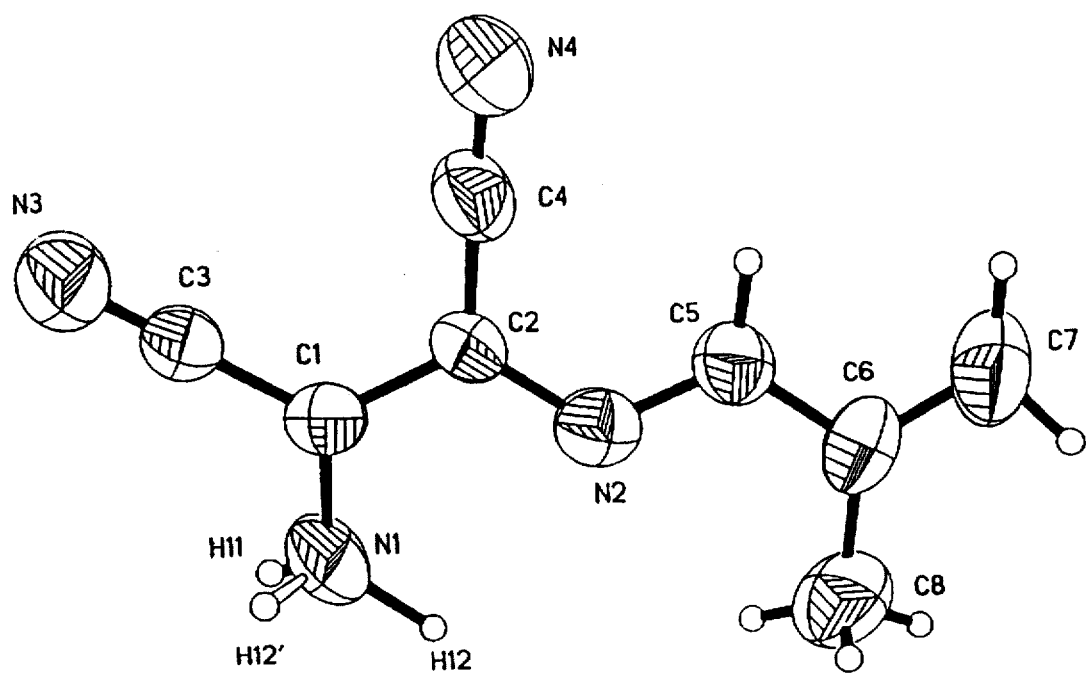
FIGS. 34 and 35 show perspective drawings of the solid state structure for $C_8H_8N_4$ (methacrodamn).

FIG. 34 shows results of crystal structure analysis for methacrodamn. Methacrodamn, a compound of the formula $C_8H_8N_4$ is yellow in color, is shaped like needles, and its A, B, and C direction lattice constants are respectively 16.614, 3.958, and 13,729. The lattice angles in the alpha, beta, and gamma direction are each 90°. Its calculated density is approximately 1.179 grams per cubic centimeter. Hydrogen atoms $H_{11}$ and $H_{12}$ were located from a difference Fourier map and refined as independent isotropic atoms. The methyl group ($C_8$ and its hydrogens) was refined as a rigid rotor with $sp^3$-hybridized geometry and a C—H bond length of 0.96 Å. The initial orientation of the methyl group was determined from difference Fourier positions for the hydrogen atoms. The final orientation of the methyl group was determined by three rotational parameters. The refined positions of the rigid rotor methyl group gave C—C—H angles which ranged from 107° to 111°. The remaining hydrogen atoms were included in the structure factor calculations as idealized atoms (assuming $sp^2$-hybridization of the carbon atoms and a C—H bond length of 0.96 Å) "riding" on their respective carbon atoms. The isotropic thermal parameters for $H_{11}$ and $H_{12}$ refined to final values of 8(2)Å$^2$ and 17(4)Å$^2$, respectively. The isotropic thermal parameter of each remaining hydrogen atom was fixed at 1.2 times the equivalent isotropic thermal parameter of the carbon atom to which it is covalently bonded. Hydrogen atoms which are covalently bonded to carbon are labeled with the same numerical subscripts as their carbon atom. The hydrogen atoms bonded to amine nitrogen $N_1$ are labelled at $H_{11}$ and $H_{12}$, respectively.

FIG. 34 shows a perspective drawing of the solid state structure for $C_8H_8N_4$ with all nonhydrogen atoms represented by thermal vibration ellipsoids drawn to encompass 50 percent of their electron density. Hydrogen atoms are represented by arbitrarily small spheres which are in no way representative of their true thermal motion. The protons of the amine nitrogen ($N_1$) appear to be disordered in the lattice with alternate protonation sites for one of the hydrogens.

Figure 35:
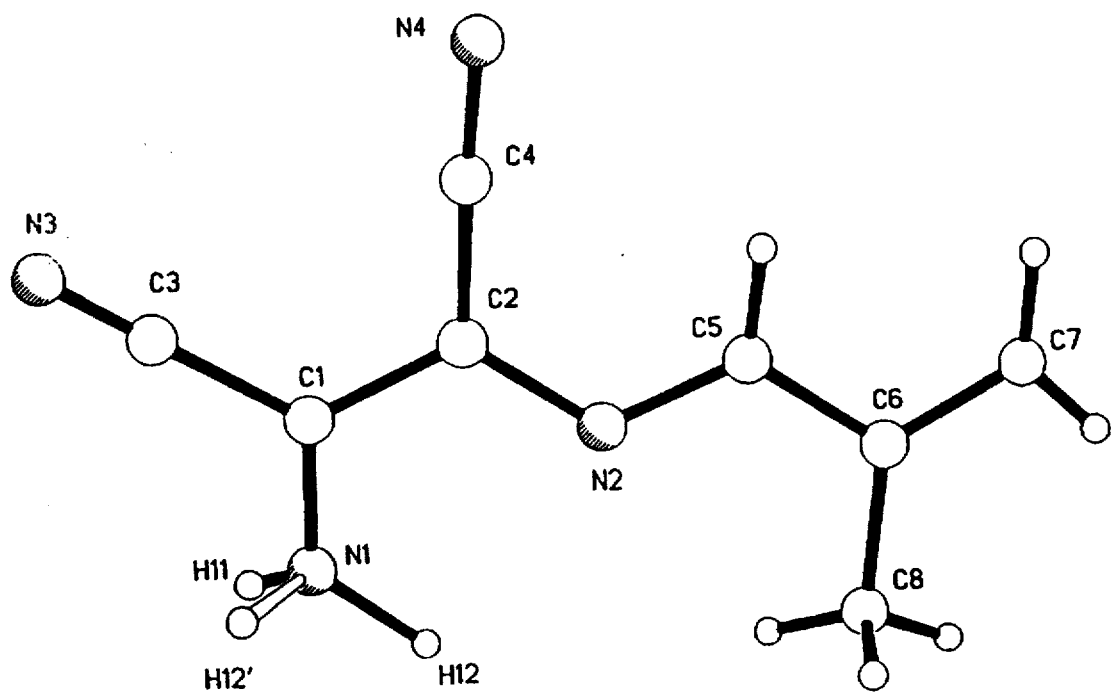

Hydrogen atoms were included at these two sites (designated as $H_{12}$ and $H_{12'}$, and shown with solid and open bonds, respectively) with occupancy factors of 0.50. FIG. 35 shows a perspective drawing of the solid state structure for $C_8H_8N_4$ with the nitrogen atoms represented by medium sized shaded spheres and carbon and hydrogen atoms represented by medium sized and small open spheres, respectively. The protons of the amine nitrogen ($N_1$) appear to be disordered in the lattice with alternate protonation sites for one of the hydrogens. Hydrogen atoms were included at these two sites (designated as $H_{12}$ and $H_{12'}$ and shown with solid and open bonds, respectively) with occupancy factors of 0.50.

Figure 36:
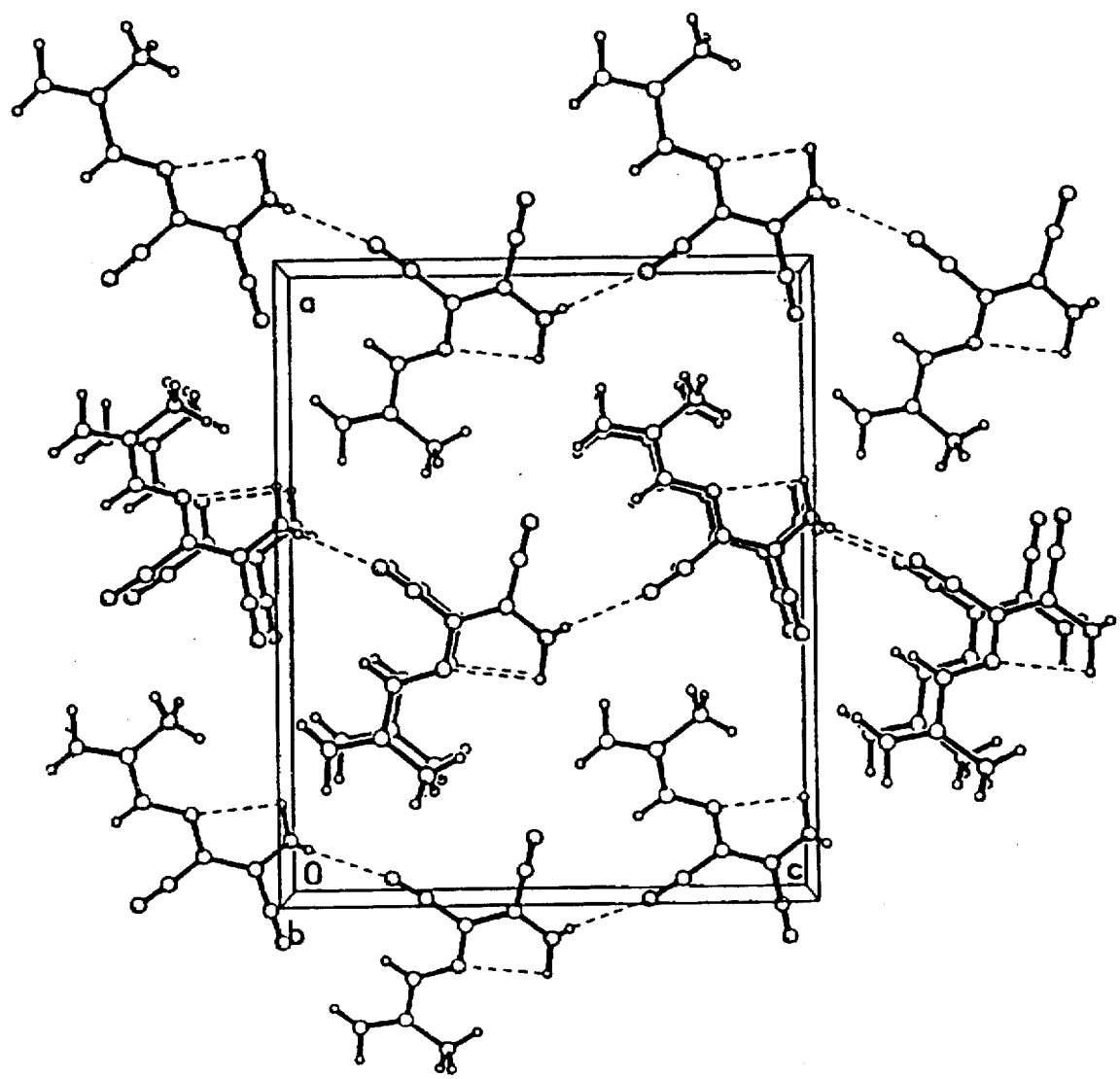
FIGS. 36, 37, and 38 show packing diagrams of the solid state structure for $C_8H_8N_4$ methacrodamn according to FIG. 35.
Figure 37:
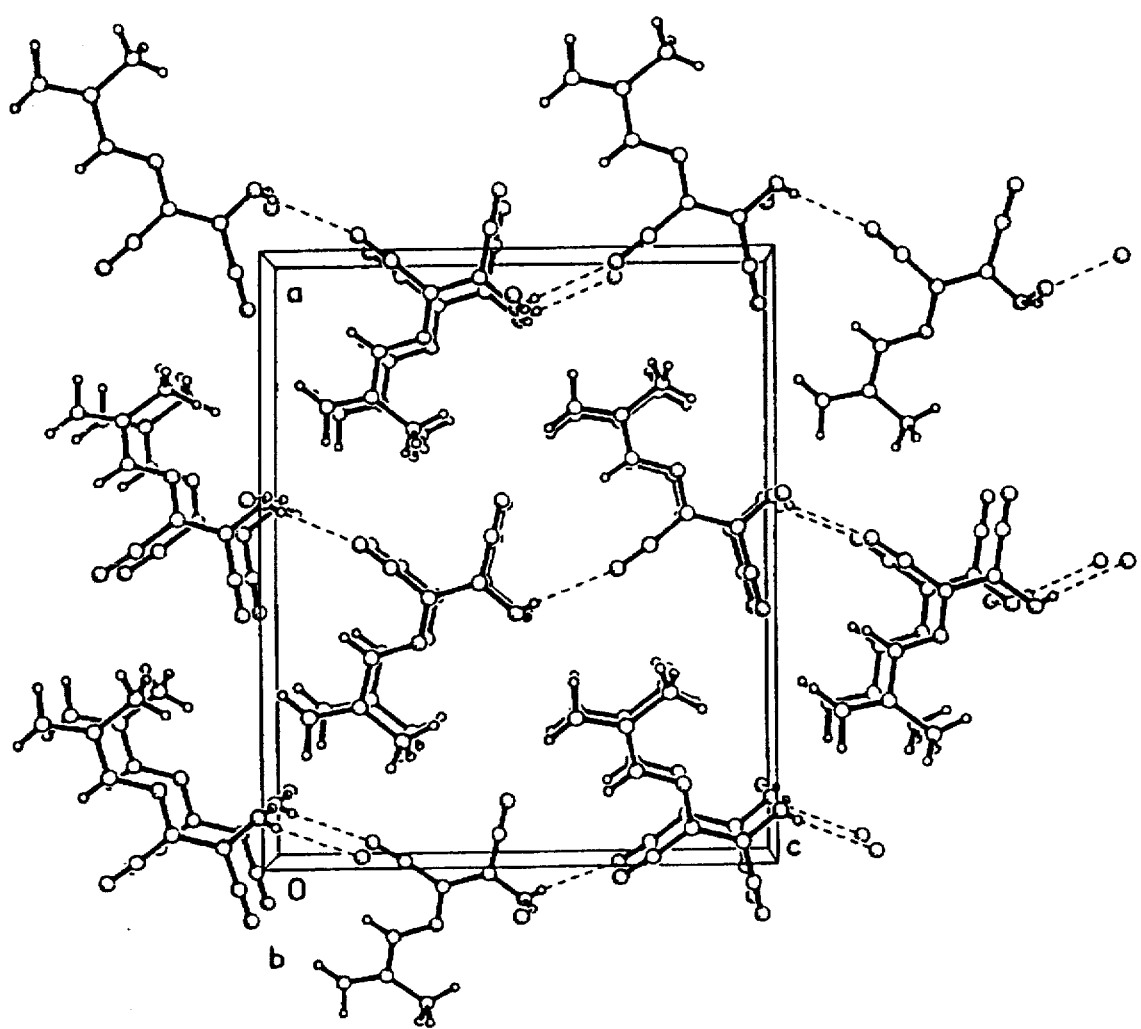
Figure 38:
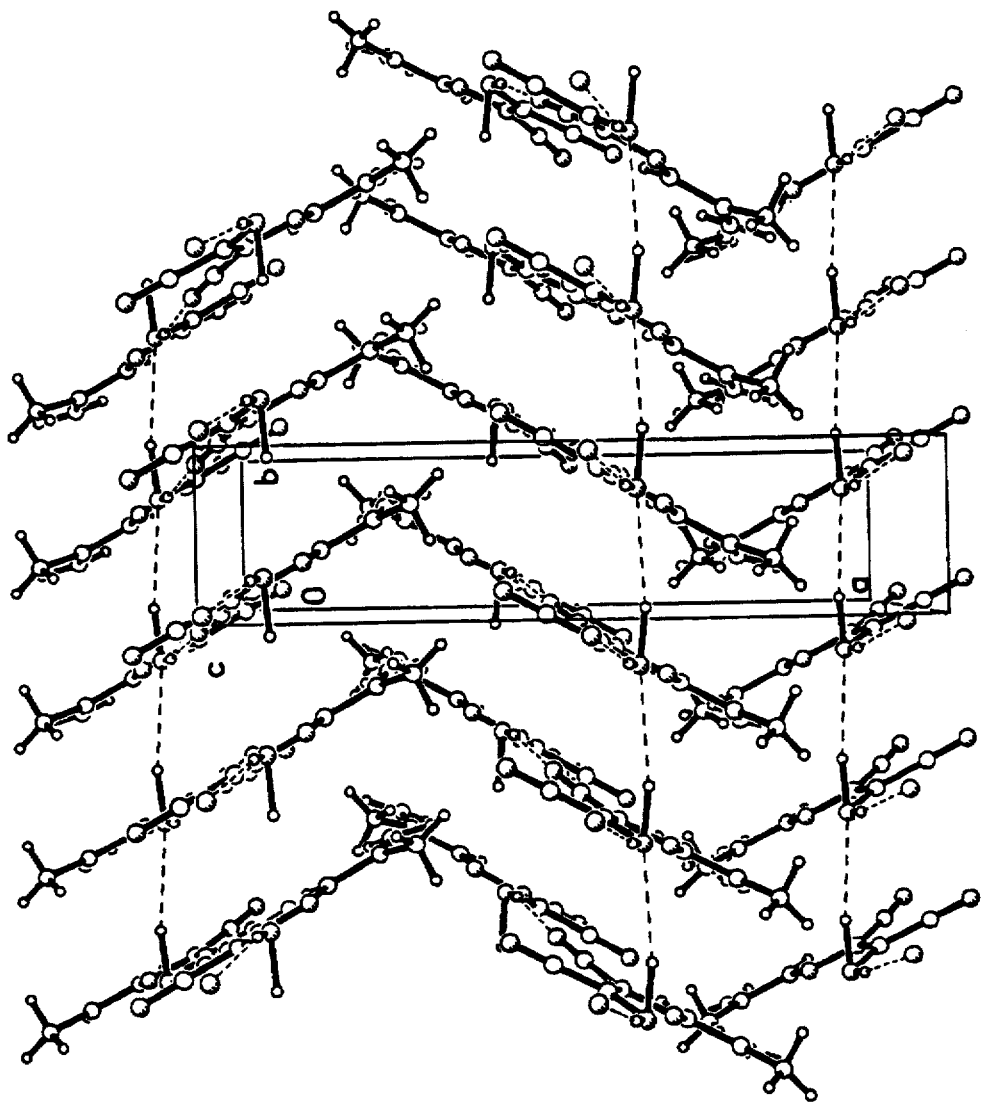

FIGS. 36 and 37 show packing diagrams of the solid state structure for $C_8H_8N_4$ viewed down at b axis with atoms represented as shown in FIG. 35. Partial occupancy hydrogen atom $H_{12'}$ has been omitted from FIG. 36 and partial occupancy atom $H_{12}$ has been omitted from FIG. 37. In both figures, the "intermolecular-intralayer" hydrogen bonding interactions involving $H_{11}$ and $N_4$ (assumed to be present all of the time) are shown with dashed lines. In FIG. 36, the intramolecular hydrogen bonding interactions involving partial occupancy hydrogen atom $H_{12}$ are also shown with dashed bonds. In FIG. 37, the intermolecular hydrogen bonding interactions (nearly parallel to the B axis) involving partial occupancy hydrogen atom $H_{12'}$ are also shown with dashed bonds. FIG. 38 shows a packing diagram of the solid state structure for $C_8H_8N_4$ viewed down the c axis with atoms represented as shown in FIG. 35. As in FIG. 37, partial occupancy hydrogen atom $H_{12}$ has been omitted and the "intermolecular—intralayer" hydrogen bonding interactions involving $H_{11}$ and $N_4$ (assumed to be present all of the time) are shown with dashed lines. The intermolecular hydrogen bonding interactions (nearly parallel to the b axis) involving partial occupancy hydrogen atom $H_{2'}$ are also shown with dashed bonds.

Hydrogen atoms $H_{11}$, $H_{12}$, $H_{12'}$, $H_{7a}$, and $H_{7b}$ were located from a difference Fourier map and refined as independent isotropic atoms. The methyl group ($C_8$ and its hydrogens) was refined as a rigid rotor with $sp^3$-hybridized geometry and a C—H bond length of 0.96 Å. The initial orientation of the methyl group was determined from difference Fourier positions for the hydrogen atoms. The final orientation of the methyl group was determined by three rotational parameters. The refined positions for the rigid rotor methyl group gave C—C—H angles which ranged from 101° to 116°. The remaining hydrogen atom ($H_5$) was included in the structure factor calculations as an idealized atom (assuming $sp^2$-hybridization of the carbon atom and a C—H bond length of 0.96 Å) "riding" on its respective carbon atom. The isotropic thermal parameters for $H_{11}$, $H_{12}$, $H_{12'}$, $H_{7a}$, and $H_{7b}$ refined to final values of $2(1)Å^2$, $6(2)Å^2$, $5(2)Å^2$, $7(2)Å^2$, and $5(2)Å^2$, respectively. The isotropic thermal parameter for each remaining hydrogen atom was fixed at 1.2 times the equivalent isotropic thermal parameter of the carbon atom to which it is covalently bonded. Hydrogen atoms which are covalently bonded to carbon are labeled with the same numerical subscript as their carbon atoms with an additional literal subscript (a, b, or c) where necessary to distinguish between hydrogens bonded to the same atom. Hydrogens bonded to nitrogen atom $N_1$ are labeled as $H_{11}$, $H_{12}$, and $H_{12'}$, respective. The protons of the amine nitrogen ($N_1$) appear to be disordered in the lattice with alternate protonation sites for one of the hydrogens. Hydrogen atoms were included at these two sites (designated as $H_{12}$ and $H_{12'}$) with occupancy factors of 0.50.

The ability to form unsaturated aldehyde derivatives of DAMN is surprising in view of failed attempts by others to produce such novel compounds. In a monograph entitled "Acrolein" edited by C. W. Smith there is a chapter by Finch regarding reactions of acrolein with nitrogen compounds, the chapter includes the following statement: "Attempts to prepare aliphatic aldimines by the reaction of acrolein with one equivalent of an amine have so far been unsuccessful; . . . " ("Acrolein," edited by Curtis W. Smith, Wiley, New York, 1962. Chapter 6, by H. D. Finch entitled "Reaction with Nitrogen Compounds.") Just such a reaction, heretofore thought impossible, is what the present invention has accomplished. Another example of "teaching away" from the invention can be found in "Synthesis of N-Allylidenealkylamines" by Pollard and Parcell appearing in June 1951 in Journal of the American Chemical Society, No. 73, 2925, 1951.

The reaction thought to be not possible, is accomplished under low temperature conditions using DAMN as the amine. Heretofore, no one has suggested or accomplished reaction of DAMN with simple unsaturated aldehydes. The acrolein is essentially a "parent" aldehyde and the methacrolein and crotonaldehyde are the 2-methyl and 3-methyl derivatives of acrolein. Other alkyl groups at these positions will allow preparation of analogous compounds by those persons skilled in the art using the teachings of the invention. However, it is suggested that the other alkyls, other than methyl or ethyl groups, be propyl, butyl, or possibly isopropyl. Larger groups with more carbon atoms, and especially more hydrogens, are thought not to be desirable insofar as thermal properties and steric hindrance associated with intermolecular separation could lead to different geometrical isomers and/or to lower stability in the solid state. Accordingly, although the invention is not limited by the preferred substituted and substituted alkyls described herein, best results are thought to occur with lower alkyls, $C_1$ to $C_4$. It is thought that any substituted or unsubstituted unsaturated aldehyde will work, so long as the length of the aldehyde compound and its substituents do not interfere with monomer formation; and do not interfere with polymerization.

Further, those skilled in the art will understand that the stoichiometric general formula illustrated for the compounds, is irrespective of the geometry that such compounds and derivatives ultimately take. Therefore, the invention is not limited by the geometry, such as cis and trans configuration as described earlier. Those skilled in the art will understand that the location and size of the alkyl groups attached to the basic molecular framework produce important differences in properties.

The method of the invention is surprisingly simple, straight forward, and gives soluble polymers in contrast to the more complex methods used for forming polymers. Accordingly, the invention provides the very desirable, Polymers adaptable for use in several possible applications. Such polymers which exhibit thermal stability are useful for many applications, such as flame resistant coatings, formation of shaped flame retardant materials, and specialty forms of carbon, for example, for purification purposes.

While this invention has been described in terms of certain embodiments thereof, it is not intended that it be limited to the above description, but rather only to the extent set forth in the following claims.

The embodiments of the invention in which an exclusive property or privilege is claimed are defined in the following claims.

We claim:
1. A compound of the formula I:

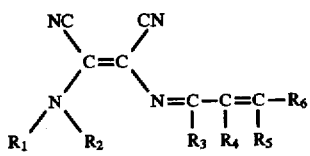

FORMULA I where $R_1$, $R_2$, $R_4$, $R_5$, and $R_6$ are identical or different and are each independently selected from hydrogen, and substituted or unsubstituted alkyl having 1 to 4 carbons, $R_3$ is hydrogen, and where at least one of said $R_1$ through $R_6$ is selected from said alkyl.

2. The compound according to claim 1 where at least one of said $R_1$ and $R_2$ is selected from said alkyls.

3. The compound according to claim 1 where at least one of said $R_4$ and $R_5$ is selected from said alkyl.

4. A compound of the formula I:

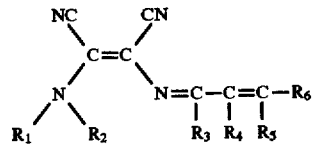

FORMULA I where $R_1$ $R_2$, $R_4$, and $R_5$, are identical or different and are each independently selected from hydrogen, and substituted or unsubstituted alkyls having 1 to 4 carbons; where one of $R_1$ and $R_2$ is an ethyl group and the other one is hydrogen; where one of $R_4$ and $R_5$ is a methyl group and the other is hydrogen; and where $R_3$ and $R_6$ are each hydrogen.

5. A compound of the formula II:

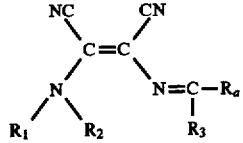

FORMULA II where $R_1$ and $R_2$ are identical or different and are each independently selected from hydrogen, and substituted or unsubstituted alkyls having 1 to 4 carbons, $R_3$ is hydrogen, and $R_a$ is an unsaturated acyclic hydrocarbon containing alternating single and double carbon bonds.

6. A compound of the formula III:

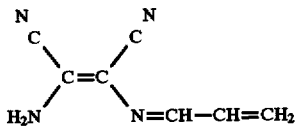

FORMULA III named acrodamn.

7. A compound of the formula IV:

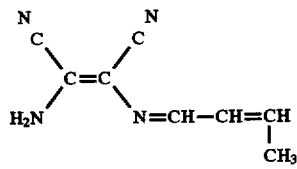

FORMULA IV named crotodamn.

8. A compound of the formula V:

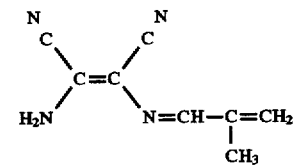

FORMULA V named methacrodamn.

* * * * *